United States Patent
Eicher et al.

(10) Patent No.: US 10,953,167 B2
(45) Date of Patent: Mar. 23, 2021

(54) SYSTEM WITH NEBULIZER AND CONTAINER

(71) Applicant: Boehringer Ingelheim International GmbH, Ingelheim am Rhein (DE)

(72) Inventors: Joachim Eicher, Ingelheim am Rhein (DE); Andreas Fiol, Norderstedt (DE); Martin Meisenheimer, Appenheim (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 0 days.

(21) Appl. No.: 15/343,343

(22) Filed: Nov. 4, 2016

(65) Prior Publication Data
US 2017/0128680 A1  May 11, 2017

(30) Foreign Application Priority Data
Nov. 6, 2015 (EP) .................................... 15020220

(51) Int. Cl.
*A61M 15/00* (2006.01)
*A61M 11/00* (2006.01)
*G01D 13/06* (2006.01)

(52) U.S. Cl.
CPC ...... *A61M 15/0073* (2014.02); *A61M 11/006* (2014.02); *A61M 11/007* (2014.02);
(Continued)

(58) Field of Classification Search
CPC ............ A61M 11/007; A61M 15/0073; A61M 15/0081; A61M 15/0065; A61M 11/006;
(Continued)

(56) References Cited

U.S. PATENT DOCUMENTS

| 3,865,279 A | 2/1975 | James |
| 4,096,945 A * | 6/1978 | Melton, Jr. ........... B05B 7/0006 206/469 |

(Continued)

FOREIGN PATENT DOCUMENTS

| EP | 0441023 A2 | 8/1991 |
| EP | 2614848 A1 | 7/2013 |

(Continued)

OTHER PUBLICATIONS

International Search Report and Written Opinion for corresponding application PCT/EP2016/076482, dated Jun. 21, 2017.
(Continued)

*Primary Examiner* — Joseph A Greenlund
*Assistant Examiner* — Steven M Cernoch
(74) *Attorney, Agent, or Firm* — Matthew B. Dernier, Esq.

(57) ABSTRACT

A system with a nebulizer as well as a container with a fluid and an indicator device for such a nebulizer are proposed. A check scheme is used for indicating the number of containers already used with the nebulizer or which still can be used with the nebulizer. The indicator device indicates the number of uses performed or still possible with the current container. The indicator device is adapted to let stepwise appear a color sequence and/or replacement symbol when approaching a predetermined number of uses with the container. Further, the indicator device can show markings in braille.

12 Claims, 24 Drawing Sheets

(52) U.S. Cl.
CPC .... *A61M 15/0065* (2013.01); *A61M 15/0068* (2014.02); *A61M 15/0081* (2014.02); *A61M 15/0071* (2014.02); *A61M 2205/582* (2013.01); *A61M 2205/584* (2013.01)

(58) Field of Classification Search
CPC ........ A61M 15/0068; A61M 2205/582; A61M 2205/584; A61M 15/0071; B05B 15/00; G01D 13/06
USPC .................................. 239/67, 68, 71, 73, 74
See application file for complete search history.

(56) References Cited

U.S. PATENT DOCUMENTS

| | | | |
|---|---|---|---|
| 5,505,195 A * | 4/1996 | Wolf | A61M 15/0045 128/200.23 |
| 6,279,759 B1 | 8/2001 | Weisbach | |
| 6,443,307 B1 | 9/2002 | Burridge | |
| 6,446,627 B1 * | 9/2002 | Bowman | A61M 15/009 128/200.23 |
| 6,606,992 B1 * | 8/2003 | Schuler | A61M 15/0028 128/203.12 |
| 6,615,827 B2 * | 9/2003 | Greenwood | A61M 15/009 128/200.23 |
| 7,185,648 B1 * | 3/2007 | Rand | A61M 15/009 128/200.23 |
| 7,621,273 B2 | 11/2009 | Morton | |
| 7,823,584 B2 | 11/2010 | Geser | |
| 8,474,447 B2 | 7/2013 | Von Schuckmann | |
| 8,550,071 B2 * | 10/2013 | Striebig | A61M 15/0045 128/203.15 |
| 8,550,074 B2 * | 10/2013 | Jones | A61M 15/0028 128/203.21 |
| 8,584,669 B2 * | 11/2013 | Besseler | A61M 15/0028 128/200.11 |
| 8,607,787 B2 * | 12/2013 | Jones | A61M 15/0088 128/203.15 |
| 8,646,446 B2 * | 2/2014 | Lewis | A61M 15/0045 128/203.12 |
| 8,887,722 B2 * | 11/2014 | Ruckdeschel | A61M 15/0045 128/203.21 |
| 9,283,336 B2 * | 3/2016 | Jones | A61M 15/0028 |
| 10,004,857 B2 * | 6/2018 | Besseler | A61M 15/0001 |
| 2002/0171238 A1 | 11/2002 | Kozlowski et al. | |
| 2003/0178020 A1 | 9/2003 | Scarrott | |
| 2005/0087191 A1 | 4/2005 | Morton | |
| 2006/0163275 A1 | 7/2006 | Stradella et al. | |
| 2006/0266842 A1 | 11/2006 | Boggs | |
| 2007/0295329 A1 | 12/2007 | Lieberman et al. | |
| 2010/0229857 A1 | 9/2010 | Von Schuckmann | |
| 2010/0294278 A1 | 11/2010 | Mosier et al. | |
| 2013/0062239 A1 | 3/2013 | Key | |
| 2015/0040893 A1 * | 2/2015 | Besseler | A61M 15/0001 128/200.21 |

FOREIGN PATENT DOCUMENTS

| | | |
|---|---|---|
| GB | 975754 | 11/1964 |
| JP | 4964286 A | 6/1974 |
| JP | 2007512856 A | 5/2007 |
| WO | 1996006011 A2 | 2/1996 |
| WO | 199639337 A1 | 12/1996 |
| WO | 2003009101 A2 | 1/2003 |
| WO | 2005041850 A1 | 5/2005 |
| WO | 2009037085 A1 | 3/2009 |
| WO | 2009115200 A1 | 9/2009 |
| WO | 02078593 A1 | 10/2010 |
| WO | 2012156725 A1 | 11/2012 |
| WO | 2012160052 A1 | 11/2012 |
| WO | 2012162305 A1 | 11/2012 |

OTHER PUBLICATIONS

Notice of Opposition for corresponding EP Patent No. 3370810, Carpmaels & Ransford, 15 pages, dated Sep. 18, 2020.

* cited by examiner

SYSTEM WITH NEBULIZER AND CONTAINER

The present invention relates to a system with a nebulizer, a container according and a check scheme to determining use of the nebulizer and when the container can or should be replaced.

WO 2012/162305 A1 discloses a nebulizer. A container can be inserted into a housing of the nebulizer. The housing is closed by a lower housing part. By rotating the housing part the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual pressing a button, the drive spring is released and moves the conveying tube into the pressure chamber so that the fluid is put under pressure by the drive spring and is delivered or atomized through a nozzle into a mouthpiece as an aerosol, without the use of propellant gas. Thus, the container is moving axially forth and back during conveying of the fluid to be nebulized, and during pressure generation and nebulization. The nebulizer comprises an indicator device for counting and/or indicating a number of uses performed or still possible. The indicator device blocks further use in a locked state when a predetermined number of uses has been reached or exceeded with the current container. Then, the container can be replaced together with a housing part and the nebulizer can be used further with the new container.

U.S. Pat. No. 7,823,584 B2 discloses a similar nebulizer, wherein a counter device can be integrated into a housing part that is exchangeable or replaceable together with the container, which is inseparable from the housing part.

US2006/0266842 A1 discloses a counter strip which is applied as a part of an adhesive label on a bottle or container to be used with an inhaler. The depicted inhaler resembles a typical metered dose inhaler ("MDI") in which the container contains not only an inhalant or liquid medication but also a propellant by which the inhalant or liquid medication is atomized. Typically such an inhaler (which typically consists of the container with an integrated metering valve and a mouthpiece with a counterpart to the metering valve of the container, the counterpart being for instance a valve stem receptacle with a nozzle bore) is completely discarded when the applicable number of dosages has been withdrawn from the container. The disclosed counter strip comprises a first and second series of numbers, indicating decades when read together. A user can use the counter strip for maintaining count of each dose taken from the container by marking through, removing, scoring or punching out a corresponding number associated with the dose. In one alternative embodiment the counter strip comprises a two layer composite of a paper with the numbers and a removable or scrape-able coating, so that the numbers get exposed when the upper layer is scraped or removed.

Object of the present invention is to provide a system with a nebulizer and a container for a nebulizer allowing easy, intuitive and/or secure operation and handling as well as a simple and/or reliable construction, in particular when the nebulizer is reused with multiple containers.

The present invention relates in particular to a system with a nebulizer for nebulizing a fluid, preferably liquid medicament, from a replaceable container containing the fluid, and relates to the container. In particular, the invention relates to a system with a nebulizer which can be reused after replacing the container, i.e. which can be used with multiple containers consecutively. Preferably, the container is detachable from the nebulizer in a nondestructive way and/or connected/attached to the nebulizer in a detachable connection, for instance in a plug-type connection which can be released by (manually) pulling the container from a holder in the nebulizer.

Preferably, an indicator device is provided for counting and/or indicating the number of uses already performed or still possible with the container.

In particular, the indicator device or an associated locking device can lock the container and/or nebulizer or can cause the locking of the container and/or nebulizer against further use in a locked state when a predetermined number of uses has been reached or exceeded with the respective container.

Preferably, the nebulizer comprises a housing part which can be detached from the nebulizer or opened for replacing the container.

According to one aspect of the present invention, the system or nebulizer comprises an associated check scheme for marking the number of containers already used or which still can be used with the nebulizer. Thus, a very secure and reliable handling can be achieved, while a very simple construction is possible. In particular, the user can see easily, preferably without the necessity to read, when the nebulizer has or is to be changed against a new nebulizer due to the number of containers used with the nebulizer. Namely, the nebulizer shall be used only for a predetermined period or total number of uses (doses) in consideration of hygienic aspects and/or mechanical wear. If the nebulizer does not have a lock which blocks automatically the nebulizer against further use if it has been used with a predetermined number of containers, the user is responsible for replacing the used nebulizer against a new one. This is highly facilitated by means of the proposed check scheme. The user can very easily and intuitively recognize when the recommended or maximum number of containers is reached or exceeded in particular as, in this case, the check scheme is full.

The proposed check scheme can be used very easily. Even users which cannot read could use the check scheme. In particular, only simple marking of the check scheme, preferably one check box after the other, is necessary to ensure an indication or overview of the number of containers already used or which still can be used with the nebulizer.

It has to be noted that the nebulizer is usually delivered without inserted container. For first use, the first container has to be inserted into the nebulizer. This insertion is preferably also considered as a "container replacement" in the sense of the present invention and is also marked on the check scheme.

Preferably, the check scheme is attached to the nebulizer. This facilitates the handling and ensures the availability of the check scheme when required, namely each time a new container is connected or inserted.

Alternatively, the check scheme could also be connected with or formed by an associated packaging, outsert or receptacle of the system or nebulizer. This allows also a very easy realization or simple construction.

Most preferably, the check scheme is attached to or formed on a housing part of the nebulizer. In particular, the housing part cannot be disconnected. Preferably, the check scheme is inseparable from the nebulizer or its housing. Thus, the desired availability of the check scheme is secure.

Preferably, the check scheme is formed on or by a label. This allows very simple construction and realization.

In particular, the check scheme or label can be used by the user to fill in the date of first use, his name and/or the like.

Preferably, the check scheme or label can be adapted to the respective drug, medical formula and/or therapy. For example, the recommended or maximum number of containers to be used with one nebulizer can vary with or depend on daily number of doses, the number of doses contained in one container, and the like.

Preferably, the check scheme comprises a check box for each of the multiplicity of containers which can be used with the nebulizer. In other words, the number of check boxes in the check scheme preferably corresponds to or is identical to the predetermined number of containers with which the nebulizer shall be used only, so that the predetermined number of total uses of the nebulizer is not exceeded. This allows very simple handling and provides a good overview of the containers already used and the remaining number of containers which still can be used with the nebulizer.

Preferably, the term "check box" has to be understood in a broad sense to cover as well other, preferably predefined check areas for marking, for example circles or the like. In particular, the check scheme comprises not more than 10 check boxes. Preferably, the check scheme comprises a number of 3 to 6 check boxes.

Preferably, the check scheme is made to be marked by writing. This allows very easy handling.

Alternatively or additionally, the check scheme can be marked by scratching. This allows also very easy handling and marking. In particular, the (detachable) housing part of the nebulizer or the new container could be used for marking so that an additional means, such as a pen or pencil, is not necessary.

Alternatively or additionally, the check scheme could be marked by tearing, cutting and/or piercing. This allows also very easy marking and/or handling.

Alternatively or additionally, the check scheme could be marked by sticking respective marks or labels (which could optionally be provided by the respective container or its packaging).

Alternatively or additionally, the check scheme or respective marks or labels could be made tactile and/or realized in braille or embossed printing so that a blind person can read the check scheme or respective marks as well.

The proposed use of a check scheme for indicating or counting the number of containers already used with the nebulizer or which still can be used with the nebulizer allows very easy handling and operation of the nebulizer. When the nebulizer is used for the first time and a container is inserted for the first time and each time the container is replaced, the check scheme or a check box thereof is marked so that it is visible when the maximum number of containers to be used with the nebulizer is approached or reached.

Preferably, the check scheme can be protected by a cover. In particular, the cover can be lifted or removed for marking the check scheme. In particular, the cover is transparent. This allows good visibility or readability of the check scheme and can prevent that marks are smeared or worn away during normal use of the nebulizer. In particular, marks marked on the check scheme or in the check boxes are protected by the cover against touching by hand of the user or any other person (even water-insoluble writing can smear or be worn away by grease of hands). Further, the cover can protect the check scheme or marks against soiling and/or humidity, in particular in bathrooms or the like.

Further, the preferred transparency of the cover can be used not only for good visibility or readability of the check scheme, but can also be used for good visibility or readability of the indicator device, preferably of an indicator device indicating and/or counting the number of uses already performed or still possible with the present container.

Preferably, the check scheme or label is arranged above or adjacent to the indicator device or its indicator element, in particular such that the user can notice or spot information of the check scheme and the indication of the indicator device simultaneously and/or without turning the nebulizer.

Preferably, the cover is formed by a housing part of the nebulizer, in particular by the housing part which has to be opened or detached for replacing the container. This allows simple and easy construction as well as intuitive handling.

According to another independent aspect of the present invention, the system, nebulizer or indicator device is adapted to let stepwise appear a color sequence and/or replacement symbol when approaching a predetermined number of uses with the container so that replacement of the container or nebulizer is necessary. This allows very easy and secure handling.

Preferably, the color sequence is used in combination with numbers. This results in a double indication which can be understood also by user which cannot read.

Preferably, the indicator device shows only part of the color sequence, in particular through a respective window or the like, so that only the relevant information is displayed. This supports secure handling and operation.

Preferably, the stepwise appearance of a replacement symbol in particular wherein the symbol approaches stepwise to a reading mark allows the user to intuitively realize when the last use of the container is approaching or coming closer even if the user is not able to read. Thus, the user is prepared to provide a new container or nebulizer.

Most preferably, the appearance of the color sequence and the appearance of the replacement symbol are combined, in particular with an appearance in a window with a precise reading mark, to allow on one hand an intuitive recognition of the rough number of uses still possible or already performed and on the other hand a (relatively) precise reading of the number of uses already performed or still possible.

According to a further independent aspect of the present invention, the indicator device may comprise a movable or rotatable indicator element with markings, a replacement symbol, numerals and/or a scale in tactile form, braille or embossed printing. Preferably, only part is visible or tactile through a window and/or appears preferably stepwise in a window. Thus, a blind person can read the indicator device as well, while allowing a simple and robust construction.

In particular, the indicator device is fixed to the container (i.e. attached to the container in such a way that it cannot be removed from the container in a nondestructive way and/or without the use of any tool). Thus, the indicator device is exchanged together with the container and the information provided by the indicator device stays with the container. This allows very easy and secure handling regarding the insertion of a container, especially as the visible replacement symbol and/or color sequence would signal the user that the container has already been (fully) used and that it should not be inserted into the nebulizer again.

Preferably the nebulizer and/or container cannot be used anymore in the locked state when the indicator device has detected that a predetermined number of uses has been reached or exceeded, in particular with the respective container.

The indicator device may either directly or indirectly lock or initiate or trigger locking of the nebulizer and/or container against further use. In particular, the indicator device may directly actuate the locking device or indirectly initiate actuation of the locking device. Preferably, the indirect actuation is realized by means or via at least partial opening of the nebulizer or its housing or housing part in order to lock the nebulizer against further use with the current container.

Preferably, the nebulizer is blocked (automatically) against further use or tensioning if the nebulizer housing or housing part is at least partially open or opened or if, with other words, when the nebulizer or its housing is not (completely) closed.

Preferably, the locking of the nebulizer against further use can be overcome by replacing the container, in particular including the indicator device, against one not yet used.

Preferably, the indicator device comprises an indicator element and an actuation element for indexing the indicator element. In particular, the indicator element displays an indication of the number of uses already performed or still possible with the respective container.

Preferably, a linear movement of the actuation element causes a rotational movement of the indicator element.

Preferably, the indicator element comprises a display with the color sequence and/or replacement symbol and/or is (only) partially visible through a window.

Preferably, the indicator element or its display show a signal color, such as red, when the recommended or maximum number of uses of the respective container and/or the locked state is approaching or reached. This facilitates intuitive handling and notice.

The above aspects of the present invention and the further aspects described below can be realized independently from each other, and in any combination.

Further advantages, features, characteristics and aspects of the present invention will become apparent from the claims and the following description of a preferred embodiment with reference to the drawings. It shows:

FIG. 1 a schematic section of a known nebulizer in a non-tensioned state;

FIG. 2 a schematic section, rotated 90° compared with FIG. 1, of the known nebulizer in a tensioned state;

FIG. 3 a schematic section of a system with a nebulizer and with an inserted container in a non-tensioned state according to a preferred embodiment of the present invention;

FIG. 4 a partial enlargement of the encircled part of FIG. 3;

FIG. 5 a perspective view of the section of the nebulizer according to FIG. 3;

FIG. 6 an enlargement of the encircled part of FIG. 5;

FIG. 7 a schematic exploded view of an indicator device according to a preferred embodiment of the present invention;

FIG. 8 an axial section of the indicator device in an actuated state;

FIG. 9 an axial section of the indicator device in a locked state;

FIG. 10 a perspective section of the indicator device in an actuated state;

FIG. 11 a perspective section of the indicator device in an released state;

FIG. 12 a partial enlargement of the nebulizer similar to FIG. 4, but in a partially tensioned state;

FIG. 13 a partial enlargement of the nebulizer similar to FIG. 4, but in a fully tensioned state;

FIG. 14 a partial section of the nebulizer similar to FIG. 4, but in an intermediate state during a dispensing stroke;

FIG. 15 a partial section of the nebulizer similar to FIG. 4, but with an indicator device of the container in a locked state;

FIG. 16 a schematic section of the nebulizer in the locked state after next tensioning with partially opened housing part and with locked locking device;

FIG. 17 a partial enlargement of the encircled part of FIG. 13;

FIG. 18 a schematic section of the nebulizer similar to FIG. 3 with unlocked locking device;

FIG. 19 a schematic section of the indicator device in the initial state according to a modified embodiment;

FIG. 20 a perspective section of the indicator device according to FIG. 19;

FIG. 21A a schematic view of the system with the nebulizer according to the preferred embodiment of the present invention with a check scheme, but without container;

FIG. 21B a schematic view of the system with the nebulizer with the check scheme similar to FIG. 21A, but with the container and indicator device;

FIG. 22 a schematic view of a modified check scheme;

FIG. 23 a schematic view of a packaging or receptacle for receiving the nebulizer and including the check scheme;

FIG. 24 a schematic view of an outsert with the check scheme;

FIG. 25 a schematic developed view of a display of the indicator device or its indicator element; and FIG. 26A-D schematic views of the container with the indicator device indicating different states.

In the Figures, the same reference numerals are used for identical or similar parts, resulting preferably in corresponding or comparable properties and advantages, even if the associated description is not repeated.

FIGS. 1 and 2 show a known nebulizer 1 for atomizing a fluid 2, particularly a highly effective pharmaceutical composition, medicament or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed or dispensed, which can be breathed in or inhaled by a user. Usually the inhaling is done at least once a day, more particularly several times a day, preferably at set intervals, depending on the complaint or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance in particular sufficient to provide up to 200 dosage units or doses, for example, i.e. to allow up to 200 sprays or applications. A typical container 3, as disclosed in WO 96/06011 A1, holds e.g. a volume of about 0.5 to 20 ml.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the total number of uses of the nebulizer 1 and thus the number of containers 3, which can be used with the same nebulizer 1, is preferably restricted, e.g. to a total number of four or five containers 3. WO 2012/162305 A1 discloses additionally such a restriction to the total numbers of containers 3 which can be used with the same nebulizer 1.

The container 3 is preferably substantially cylindrical or cartridge-shaped and once the nebulizer 1 has been opened the container 3 can be inserted therein preferably from below and changed if desired.

The container 3 is preferably of rigid construction, the fluid 2 in particular being held in a collapsible bag 4 in the container 3. In particular, the container 3 comprises a venting opening or hole 23 which is opened before or during first use.

Preferably, the fluid 2 is not under pressure in the container 3 and/or propellant-free.

The nebulizer 1 comprises a delivery mechanism, preferably a pressure generator 5, for conveying and nebulizing the fluid 2, particularly in a preset and optionally in an adjustable dosage amount.

The nebulizer 1 or pressure generator 5 comprises preferably a holder 6 for releasably holding the container 3, a drive spring 7 associated to the holder 6, only partly shown, and/or a blocking element 8 preferably in form of or with a button for preferably manual actuation or depressing. The blocking element 8 can catch and block the holder 6 and can be manually operated to release the holder 6 allowing drive spring 7 to expand.

The nebulizer 1 or pressure generator 5 comprises preferably a conveying element, such as a conveying tube 9, a non-return valve 10, a pressure chamber 11 and/or an nozzle 12 for nebulizing the fluid 2 into a mouthpiece 13.

The completely inserted container 3 is fixed or held in the nebulizer 1 via the holder 6 such that the conveying element fluidically connects the container 3 to the nebulizer 1 or pressure generator 5. Preferably, the conveying tube 9 penetrates into the container 3.

The nebulizer 1 or holder 6 is preferably constructed so that the container 3 can be exchanged.

The preferably releasable connection between the container 3 and the holder 6 can be in the form of a plug-in connection, a screw connection or a bayonet connection.

Preferably, the connection between the container 3 and the holder 6 is a plug-type connection in which the holder 6 comprises a plurality of snap hooks which engage into a peripherally extending groove in the container 3 or in an outer casing of the container 3 after the container has been inserted into the nebulizer 1.

When the drive spring 7 is axially tensioned in the tensioning process, the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the blocking element 8 so that the drive spring 7 is kept compressed. Then, the nebulizer 1 is in the tensioned state.

During the subsequent relaxation in the nebulization process after actuation or pressing of the blocking element 8 the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1, and, thus, dispensed.

Generally, the nebulizer 1 operates with a spring pressure of 5 to 300 MPa, preferably 10 to 250 MPa on the fluid 2, and/or with a volume of fluid 2 delivered per stroke of 10 to 50 µl, preferably 10 to 20 µl, most preferably about 15 µl.

The fluid 2 is converted into or nebulized as aerosol 14, the droplets of which have an aerodynamic diameter of up to 20 µm, preferably 3 to 10 µm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

The nebulizer 1 comprises preferably a housing 24 and/or (upper) housing part 16 and optionally a biasing or inner part 17 preferably which is rotatable relative thereto (FIG. 2) and/or has an upper part 17a and a lower part 17b (FIG. 1).

The nebulizer 1 or housing 24 comprises preferably a (lower) housing part 18. This part 18 is in particular manually operable, and/or releasable fixed, particularly fitted or held onto the inner part 17, preferably by means of a retaining element 19.

Preferably, the housing parts 16 and 18 and/or other parts form the housing 24 of the nebulizer 1.

In order to insert and/or replace the container 3, preferably the housing 24 can be opened and/or the housing part 18 can be detached from the nebulizer 1, inner part 17 or housing 24.

Generally and preferably, the container 3 can be inserted before the housing 24 is closed and/or before the housing part 18 is connected to the housing 24. The container 3 may be inserted, opened and/or fluidically connected to the delivery mechanism automatically or simultaneously when (completely) connecting the housing part 18 to the housing 24/nebulizer 1 and/or when (completely) closing the housing 24/nebulizer 1. Preferably, the container 3 is open or fluidically connected when tensioning the nebulizer 1 for the first time with the current container 3.

Preferably, the nebulizer 1 or drive spring 7 can be manually activated or tensioned or loaded, in particular by actuation of an actuation member, here preferably by rotating housing part 18 or any other component.

The actuation member, preferably the housing part 18, can be actuated, here rotated relative to the upper housing part 16, carrying with it or driving the inner part 17. The inner part 17 acts on a gear or transmission to transform the rotation in an axial movement. As a result the drive spring 7 is tensioned in the axial direction by means of the gear or transmission (not shown) formed between the inner part 17, in particular its upper part 17a, and the holder 6 and acting on the holder 6. During tensioning the container 3 is moved axially downwards until the container 3 assumes an end position as shown in FIG. 2. In this activated or tensioned state the drive spring 7 is under tension and can be caught or held by the blocking element 8. During the nebulizing process the container 3 is moved back into its original position (non-tensioned position or state shown in FIG. 1) by (the force of) the drive spring 7. Thus the container 3 executes a lifting or stroke movement during the tensioning process and during the nebulizing process.

The housing part 18 preferably forms a cap-like lower housing part and/or fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal or foil 50 thereon with a piercing element 22 when the container 3 makes contact with it for the first time, to allow air in or aeration, preferably by opening or piercing venting hole 23. The venting hole 23 allows for pressure compensation inside the container 3 when fluid 2 is drawn from the container 3 during the actuation of the nebulizer 1.

The nebulizer 1 comprises preferably an indicator device 25, which counts in particular actuations of the nebulizer 1, preferably by detecting its tensioning or the rotation of the inner part 17 relative to the upper part 16 or housing 24. Preferably, the counter device 25 or an associated locking device 26 locks the nebulizer 1 against (further) actuation or use, e.g. blocks further rotation of the housing part 18/inner part 17 and, thus, tensioning of the nebulizer 1 or its drive spring 7 and/or blocks actuation of the blocking element 8, in a locked state when a certain number of actuations or operations or discharged doses has been reached or exceeded.

In the following and with reference to the further figures, a preferred embodiment of the nebulizer 1, container 3, indicator device 25 and/or locking device 26 is described and shown according to the invention, wherein primarily important aspects and differences will be described and the previous aspects, features and explanations apply preferably additionally or correspondingly even without repetition.

The present invention relates in particular to a system 100 for nebulizing a fluid 2, wherein the system 100 comprises the nebulizer 1 and optionally the container 3 and/or indicator device 25.

FIG. 3 shows the system 100 with the nebulizer 1, with the container 3 and the indicator device 25 according the present invention in a schematic section (longitudinal section) in the non-tensioned state with completely closed nebulizer housing 24 and, thus, closed housing part 18, wherein the container 3 including the proposed indicator device 25 are inserted into or received within the nebulizer 1 and/or housing 24.

FIG. 4 shows an enlarged partial section of the encircled part of FIG. 3. FIG. 5 shows a perspective view of the section of the nebulizer 1 of FIG. 3. FIG. 6 shows a partial enlargement of the encircled part of FIG. 5.

The nebulizer 1 has preferably a longitudinal form or axis which corresponds to the axial direction and/or to the main dispensing direction and/or to stroke movement of the container 3 during tensioning and dispensing.

In the shown non-tensioned state, the nebulizer 1 or its mouthpiece 13 is preferably closed by a mouthpiece cover 27. The mouthpiece cover 27 is preferably pivotable to allow opening of the mouthpiece 13 for using the nebulizer 1.

Preferably, the indicator device 25 is directly and/or unreleasably secured or fixed to or connected with the container 3. In particular, the indicator device 25 is associated to a respective container 3. If the container 3 of the nebulizer 1 is replaced, the indicator device 25 is necessarily or positively replaced as well.

Preferably, the indicator device 25 is fixedly arranged at the bottom or container base 21 of the container 3 and/or opposite to an outlet or head 28 of the container 3.

In the present embodiment, the indicator device 25 is preferably directly connected to or abuts at an outer case or preferably rigid housing 29 of the container 3.

Preferably, the indicator device 25 and the container 3 are connected by form-fit and/or snap-fit.

In particular, the indicator device 25 circumvents and/or grips over a (lower or bottom) edge 30 and/or any other protrusion or the like of the container 3. In the present embodiment, the edge 30 is a little bit wider in diameter so that it protrudes radially over the essentially cylindrical outer form of the side wall of the container 3/container housing 29.

The diameter of the indicator device 25 is preferably at least essentially equal to or slightly greater than the diameter of the container 3 or its edge 30.

The edge 30 is preferably formed between the side wall and the bottom or base 21 of the container 3 or container housing 29. Preferably, the edge 30 is formed by flanging, bordering, bending or crimping or by any other suitable material-deforming process.

The indicator device 25 comprises a housing 31 and/or preferably has an at least essentially cylindrical form.

The indicator device 25 or its housing 31 is preferably attached to the container 3 or its base 21 or housing 29 with an at least essentially flat and/or axial side.

The indicator device 25 or its housing 31 comprises preferably a holding or gripping section 32 for connecting the indicator device 25 with the container 3. Preferably, the gripping section 32 circumvents the edge 30 and/or grips around or over the edge 30.

In the present embodiments, the gripping section 32 is preferably annular and/or grips over the edge 31 at positions distributed over the circumference of the edge 30 or container 3.

Preferably, the indicator device 25 and the container 3 are connected with each other by a snap-fit or click connection. Preferably, the container 3 and the indicator device 25 are connected with each other by axially snapping one part on the other.

Preferably, the gripping section 32 is sufficiently elastic in radial direction so that the container 3 can be entered axially with its edge 30. In the present embodiment, the gripping section 32 preferably comprises a respectively inclined insertion face to facilitate insertion of edge 30 into the annular gripping section 32 or between circumferentially distributed gripping sections 32.

It has to be noted that other constructional solutions are possible for connecting the container 3 or its housing 29 with the indicator device 25 or its housing 31 or vice versa. In particular, the two parts can be connected with each other additionally or alternatively by welding, brazing, gluing, screwing, clamping, hot-pressing, or the like.

FIG. 7 shows in a schematic, exploded view the indicator device 25 according to the preferred embodiment of the present invention.

The indicator or its housing 31 comprises preferably an upper part 33 and a lower part 34.

Preferably, the upper part 33 holds or forms the gripping section 32.

The indicator device 25 comprises preferably an indicator element 35 and an associated actuation element 36 and/or a transmission 40 or gear 41 for indexing the indicator element 35 or for causing the indexing of the indicator element 35.

The indicator device 25 is for counting and/or indicating a number of uses performed or still possible with the respective or associated container 3. Preferably, the indicator element 35 comprises markings 37, such as one or more symbols, numbers, coloured or shaded areas or the like, for at least roughly indicating the number of uses already performed with or still possible with the respective container 3. In the present embodiment, the indicator element 35 is preferably rotatable and/or comprises a circumferential wall or outer surface with the at least one marking 37.

The indicator housing 31 comprises preferably a window 31*a*, in particular in the circumferential wall through the relevant marking 37 is visible for a user or patient, preferably through the housing part 18 which is in particular transparent.

The actuation element 36 comprises preferably an actuation arm 38 which, intern comprises preferably a free or actuation end 39, for direct or indirect actuation or indexing of the indicator element 35. Indexing means that the indicator element 35 is moved forward in increments or steps.

Preferred is an indirect actuation or driving so that the actuation element 36 or its arm 38 actuates or drives the indicator element 35 via a transmission 40. In the present embodiment, the transmission 40 results in a reduction and/or is realized as a worm device.

The indicator device 25 or transmission 40 comprises preferably a gear 41 and/or a worm 42. Most preferably, the worm 42 is directly formed by the gear 41 so that the gear 41 forms a worm gear and preferably comprises radially protruding teeth 43 in which at least one convolution of the worm 42 is formed (compare the horizontal or axial sections of the mounted indicator device 25 shown in FIGS. 8 and 9).

The gear 41 comprises preferably an axle, in particular one or more axle sections 44 which may axially protrude on opposite sides as realized in the present embodiment.

The actuation element 36 causes a rotation of the gear 41 around an axis preferably perpendicular to the direction of movement of the actuation element 36, the axis preferably being arranged in a horizontal plane identical or parallel to the plane given by the movement of the actuation element 36.

The gear 41 is rotatably held preferably by the housing 31 or lower housing part 34, preferably by two bearing sections 45 of the lower part 34. Preferably, the bearing sections 45 comprises recesses for rotatably holding the axle sections 44. However, other constructional solutions are possible as well.

The housing 31 or lower part 34 bears preferably the indicator element 35 such that it can rotate. In the present embodiment, the lower part 34 comprises preferably two bearing portions 46 arranged on opposite radial sides and axially protruding for rotatably bearing the indicator element 35. The actuation element 35 and/or transmission 40 are preferably arranged at least essentially in between the bearing portions 46.

The indicator device 25 comprises preferably an actuation spring 47, in particular for biasing the actuation element 36 into a preferred direction and/or for driving the indicator element 35

Figure 8:
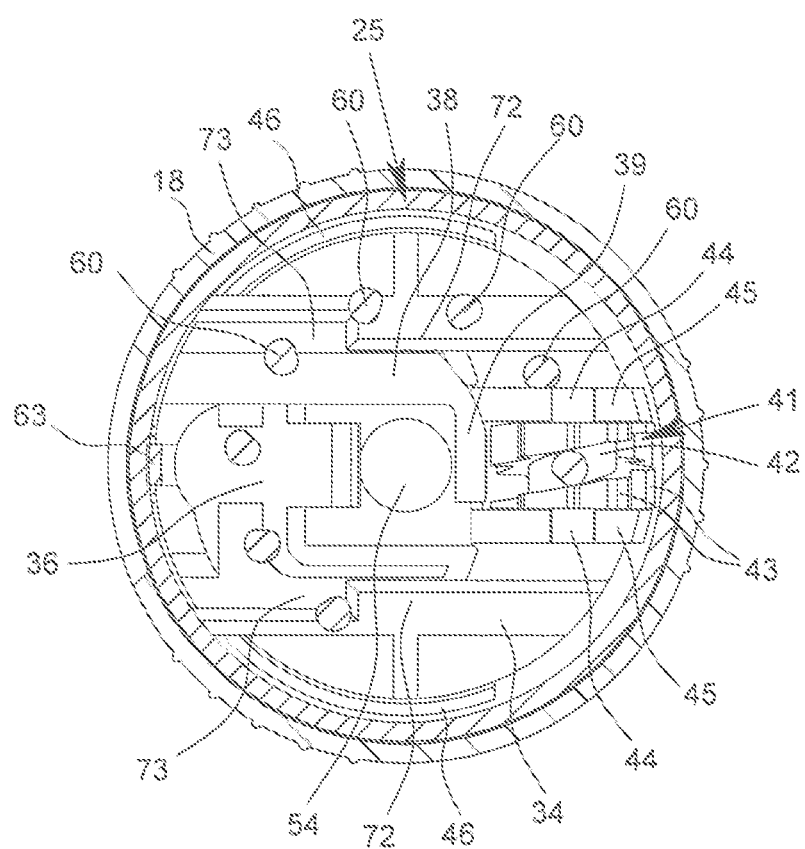
FIG. 8 shows in a horizontal or axial section the mounted indicator device 25 in an actuated state where the actuation element 36 has been moved or pushed sidewards, namely starting from the first position shown in FIGS. 3 to 6 towards the left into a second position which is shown in FIG. 8.
Figure 9:
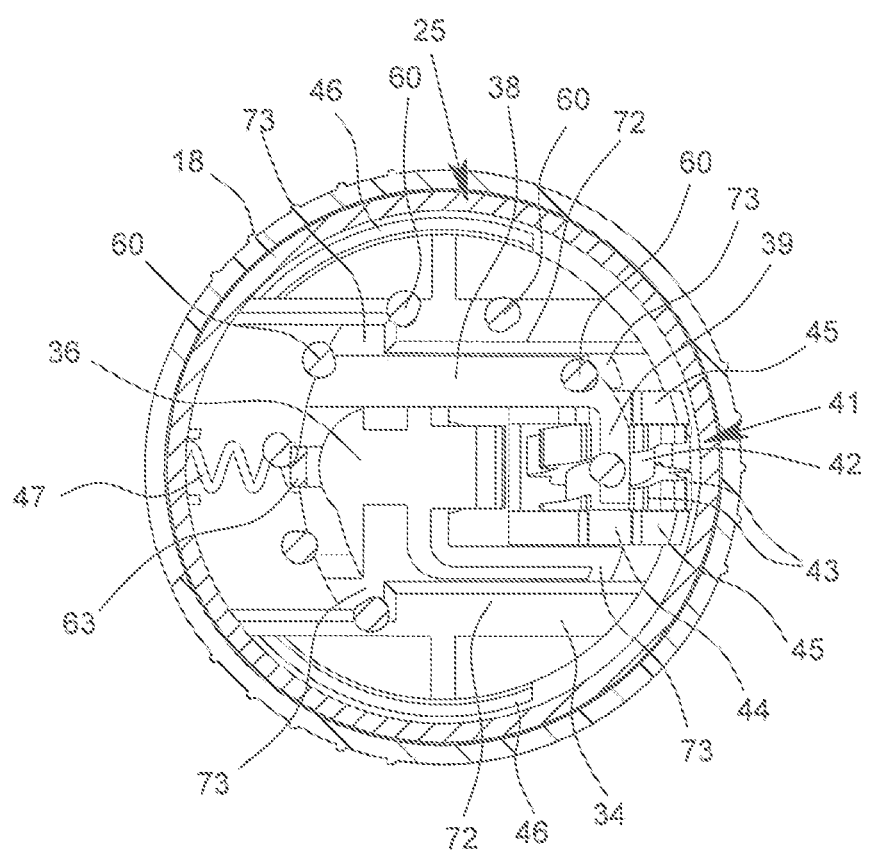
FIG. 9 shows in a similar section as FIG. 8 the indicator device 25 in a locked state where the actuation element 36 is in a locked, third position.

It can been seen from FIGS. 8 and 9 that protrusions 60 of the indicator element 35 (not shown in FIGS. 8 and 9) extend axially, wherein always at least one protrusion 60 is caught in the worm 42 so that a worm drive is formed between the gear 41 and the indicator element 35. Thus, any rotation of gear 41 is transformed in a reduced rotation of the indicator element 35. Further, a permanent engagement between the gear 41 and the indicator element 35, more precisely between at least one protrusion 60 and the worm 42, is ensured. However, other constructional solutions or couplings between the gear 41 and the indicator element 35 are possible.

Figure 10:
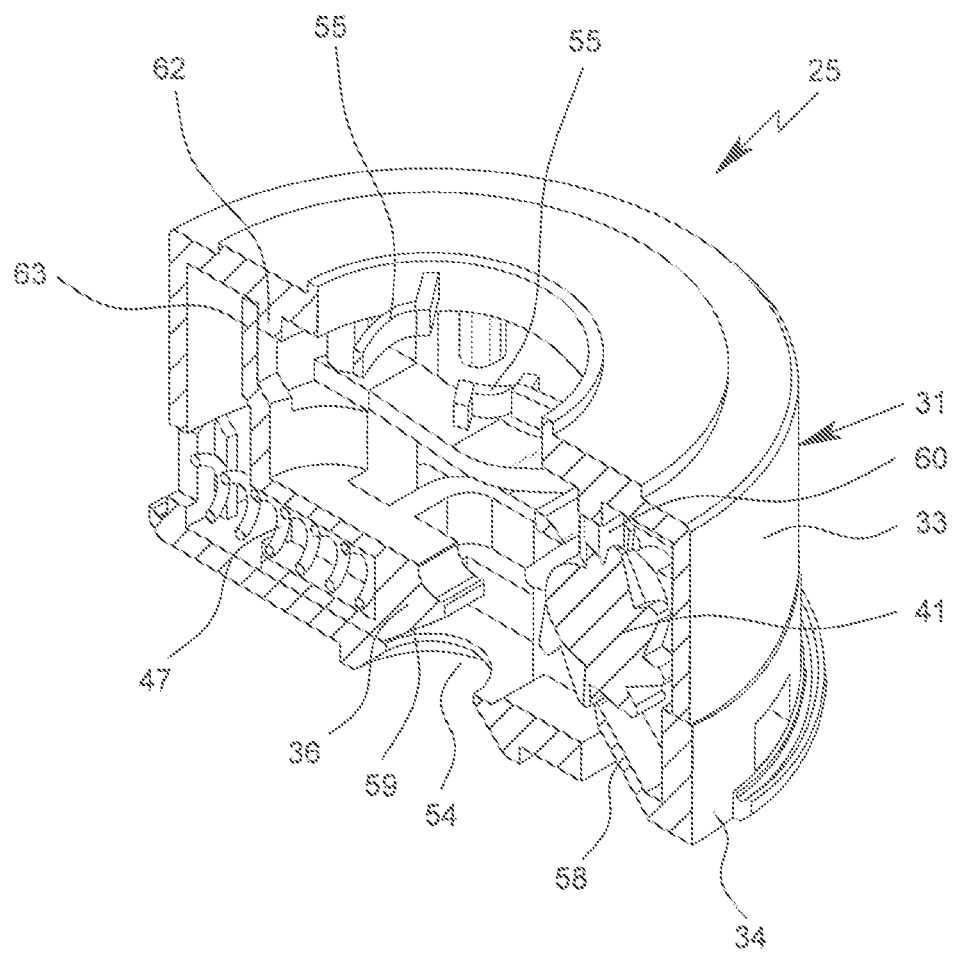
Figure 11:
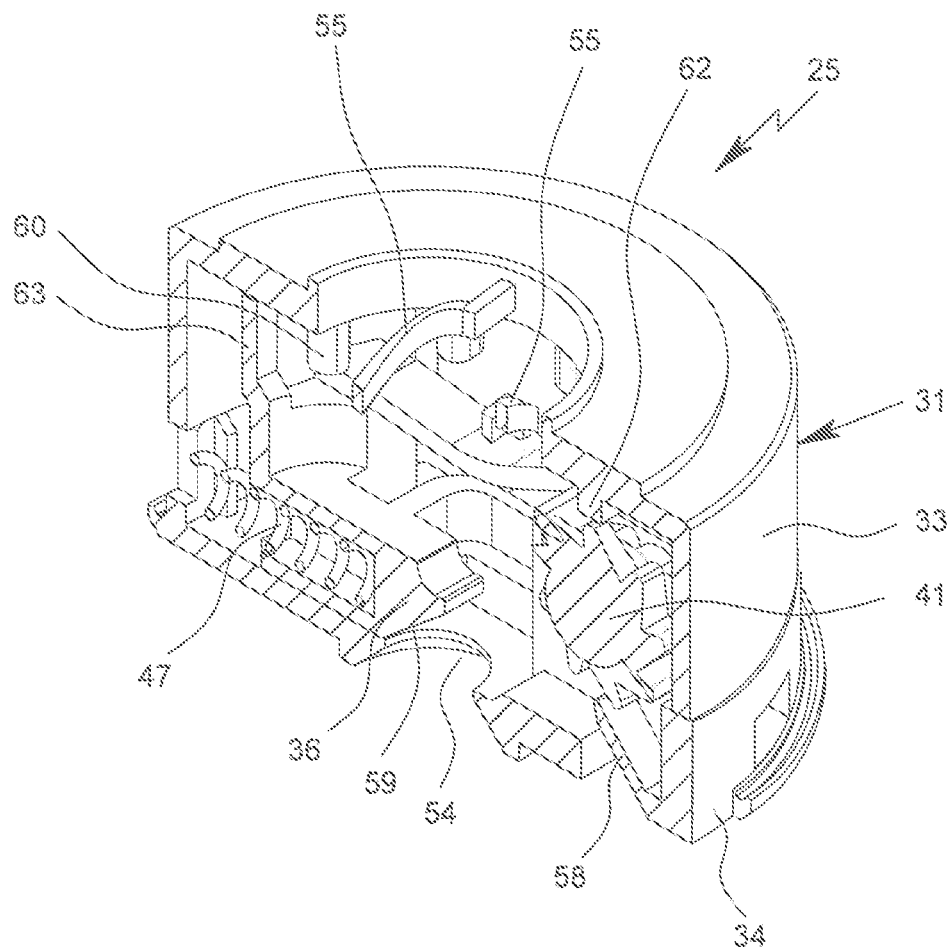

FIG. 10 shows the mounted indicator device 25 in a perspective section in the initial, first position and state. FIG. 11 shows the indicator device 25 in a similar perspective section, but with released actuation element 36, i.e. just before the locked state is reached.

Preferably, the transmission 40 or gear 41 forms a worm (helical groove) 42 with at least one convolution, preferably a with about 1.5 or more convolutions, so that always at least one engaging element of the indicator element 35 or of any other transmission component, in particular the inwardly or axially projecting protrusion 60, engages in the worm 42. Thus, rotation of the gear 41 around its preferably transversal axis results in a rotation of the indicator element 35 around its preferably longitudinally oriented rotation axis. However, other constructional solutions are possible as well.

Preferably, the teeth 43 are relatively long and/or extend radially sufficiently so that the protrusions are securely guided within the convolutions of the worm 42, in between the teeth 43, and that the actuation portion 39 can still move in radial direction between the protrusion 60 engaging into the worm 42 and the gear 41 in order to actuate or rotate the gear 41 in the desired manner. For this purpose, the actuation portion 39 may engage into respectively deep cut outs between the teeth 43 in order to be able to move below the respective projection 60.

The indicator device 25 comprises preferably a piercing part 48 (compare FIGS. 3 to 6).

The piercing part 48 is arranged within the indicator device 25 or its housing 31.

The piercing part 48 is preferably axially moveable.

The piercing part 48 is preferably moveable such that it can protrude towards the container 3 and/or can open an aeration opening, preferably the venting hole 23, of the container 3, in particular by breaking or piercing a foil 50 covering the venting hole 23.

In the present embodiment, the piecing element 48 comprises preferably an opening end or tip 49 which can open or pierce the foil 50 covering the container base 21, in particular an indention 51 formed in the container 3 or its base 21. Preferably, the indention 51 comprises a break through which forms the venting hole 23. However, other constructional solutions are possible as well.

Figure 4:
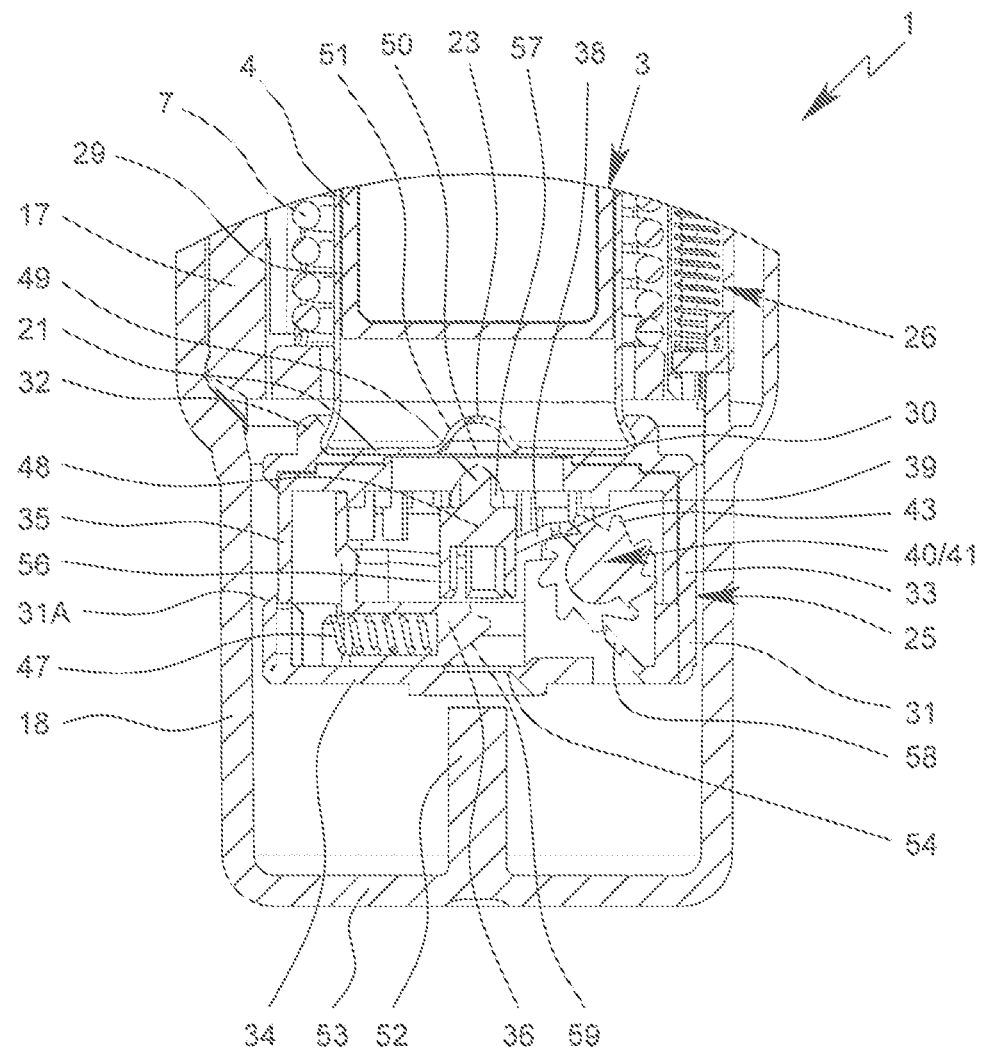
Figure 5:
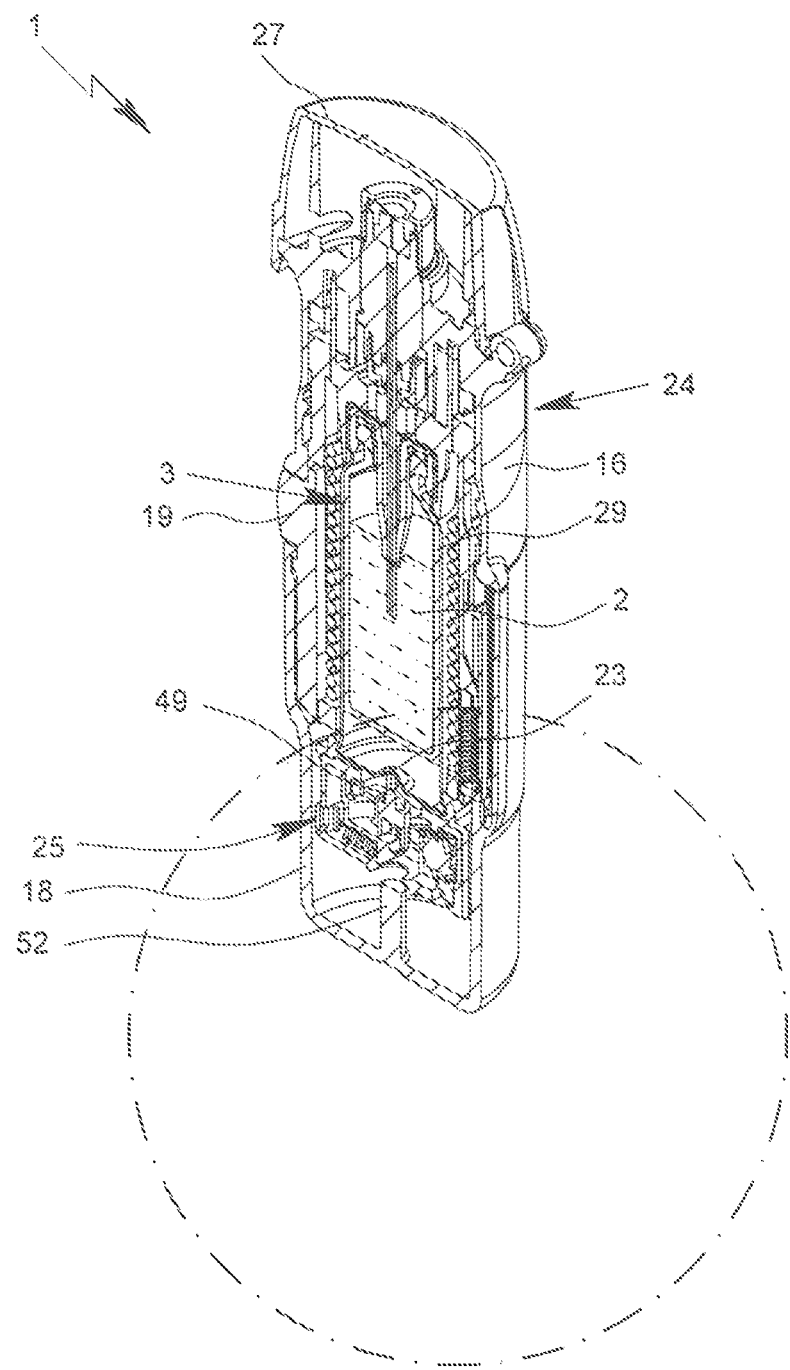
Figure 6:
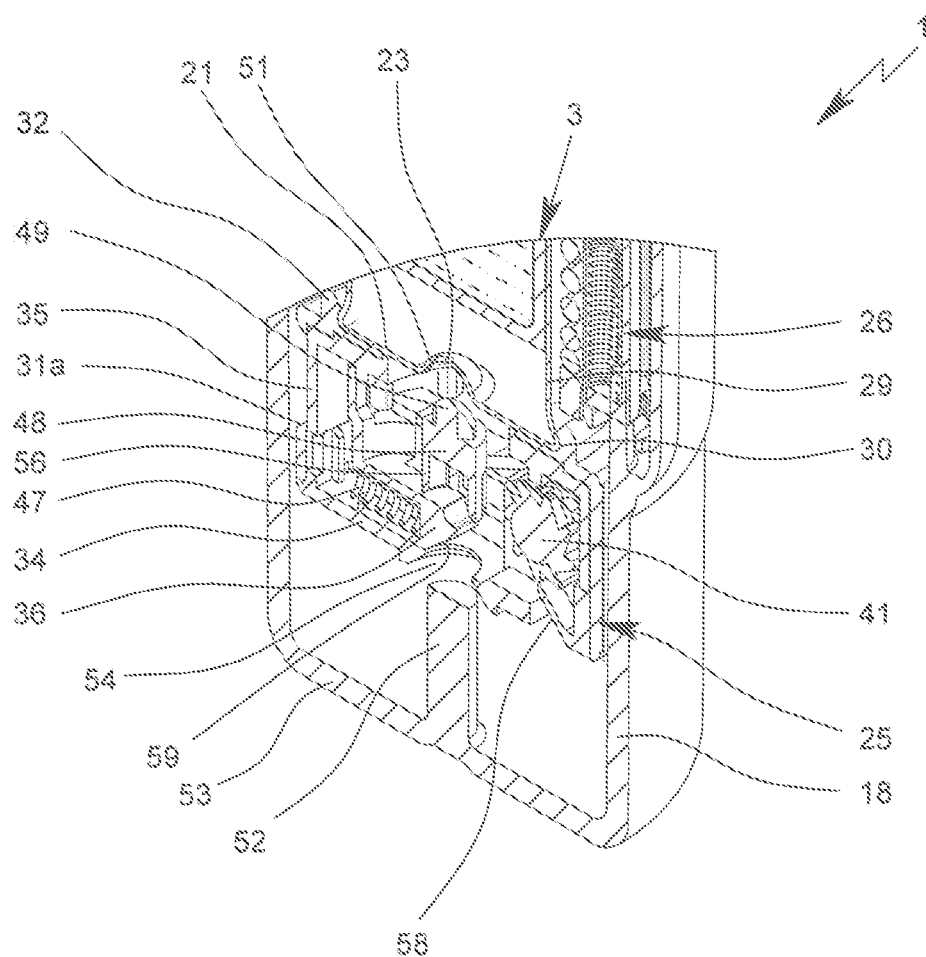
Figure 7:
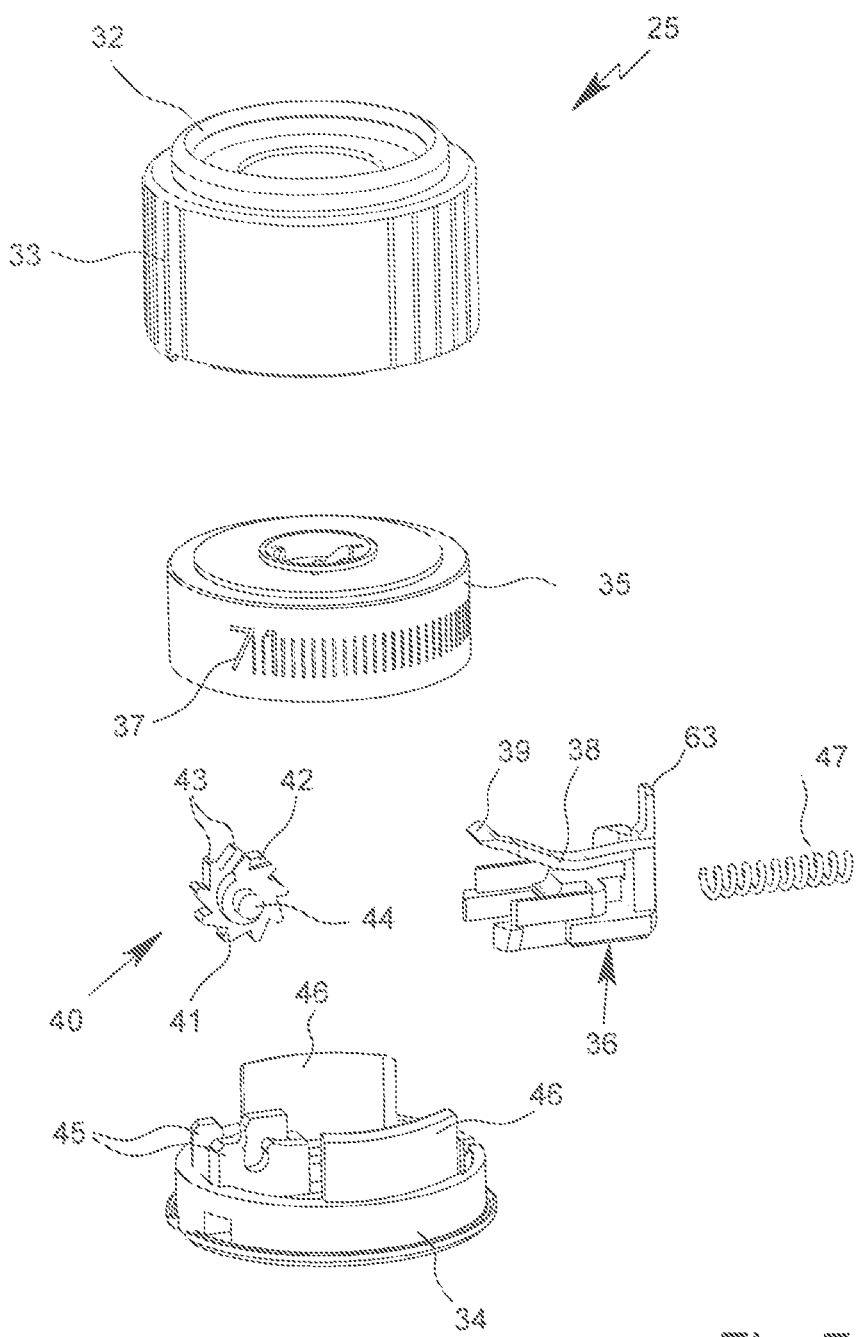
Figure 12:
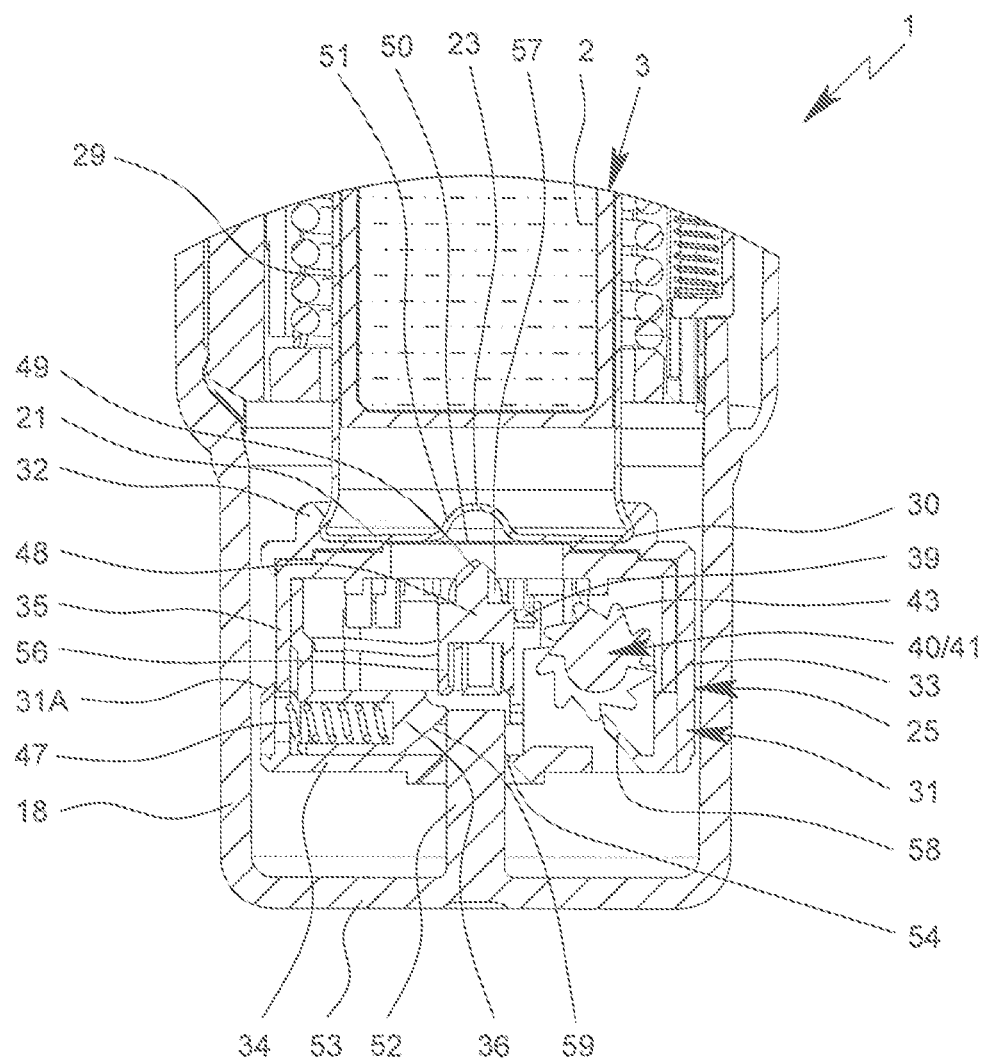

FIG. 12 shows in a partial enlargement similar to FIG. 4 a lower portion of the nebulizer 1 in an intermediate state after partial tensioning. The indicator device 25 is in an actuated state as shown in FIG. 8 (second position).

The nebulizer 1 or housing part 18 comprises preferably a driving part 52 for driving or actuating the indicator device 25 when using the nebulizer 1, in particular for actuating the indicator device 25 in response to any tensioning of the nebulizer 1 and/or any (axial or stroke-like) movement of the container 3.

Preferably, the driving part 52 is arranged or formed in the housing part 18, in particular on the axial end face or bottom 53 of the housing part 18.

Preferably, the driving part 52 is arranged centrally and/or extends axially.

Preferably, the driving part 52 is at least substantially cylindrical and/or pin-like or bolt-like.

Preferably, the driving part 52 is held by the housing part 18 and/or integrally formed by the housing part 18.

In the preferred embodiment, the movement of the container 3 and, thus, of the indicator device 25 during the tensioning (downward movement in the drawings) and/or during pressurization and dispensing (upward movement in the drawings) and/or one or both of the respective end positions in the non-tensioned state and tensioned state, respectively, can be used for actuating the indicator device 25, i.e. for counting.

Preferably, the relative movement of the container 3 and/or indicator device 25 within the nebulizer 1, and more preferred the movement during dispensing, is used for actuating or triggering the indicator device 25 and/or counting.

When tensioning the nebulizer 1 and/or moving the indicator device 25 downwards, the driving part 25 enters or engages through an insertion opening 54 of the indicator device 25 or its housing 31, in particular axially.

Preferably, the driving part 52 and the insertion opening 54 are arranged centrally and/or axially aligned.

In the present embodiment, the driving part 52 actuates the actuation element 36, i.e. moves the actuation element 36 from an initial first position shown in FIGS. 3 to 6, to an actuated second position shown in FIG. 9.

Preferably, the actuation spring 47 biases the actuation element 36 into the first position.

In the present embodiment, the actuation element 36 is moveable back and forth between the first and second positions for indexing the indicator element 35, in particular for incrementally rotating the gear 41 in one direction to respectively drive the indicator element 35. As any rotation of gear 41 is transformed in a reduced rotation of the indicator element 35, thus every movement of the actuation element 36 from the first to the second position or vice versa results in a movement of the indicator element 35.

In the present embodiment, the actuation element 36 is moveable transversally, preferably perpendicularly, to the longitudinal or dispensing direction of the container 3 or nebulizer 1 and/or to the stroke movement of the container 3 and/or indicator device 25.

Preferably, the actuation element 36 is moved from the more central first position radially outwards to the second position, in particular against the force of the associated, preferably helical actuation spring 47 biasing the actuation element 36 in opposite direction.

In the second position, the actuation element 36 has been moved with its actuation arm 38 or actuation portion 39 out of engagement with gear 41 as indicated in FIGS. 8 and 12.

Figure 13:
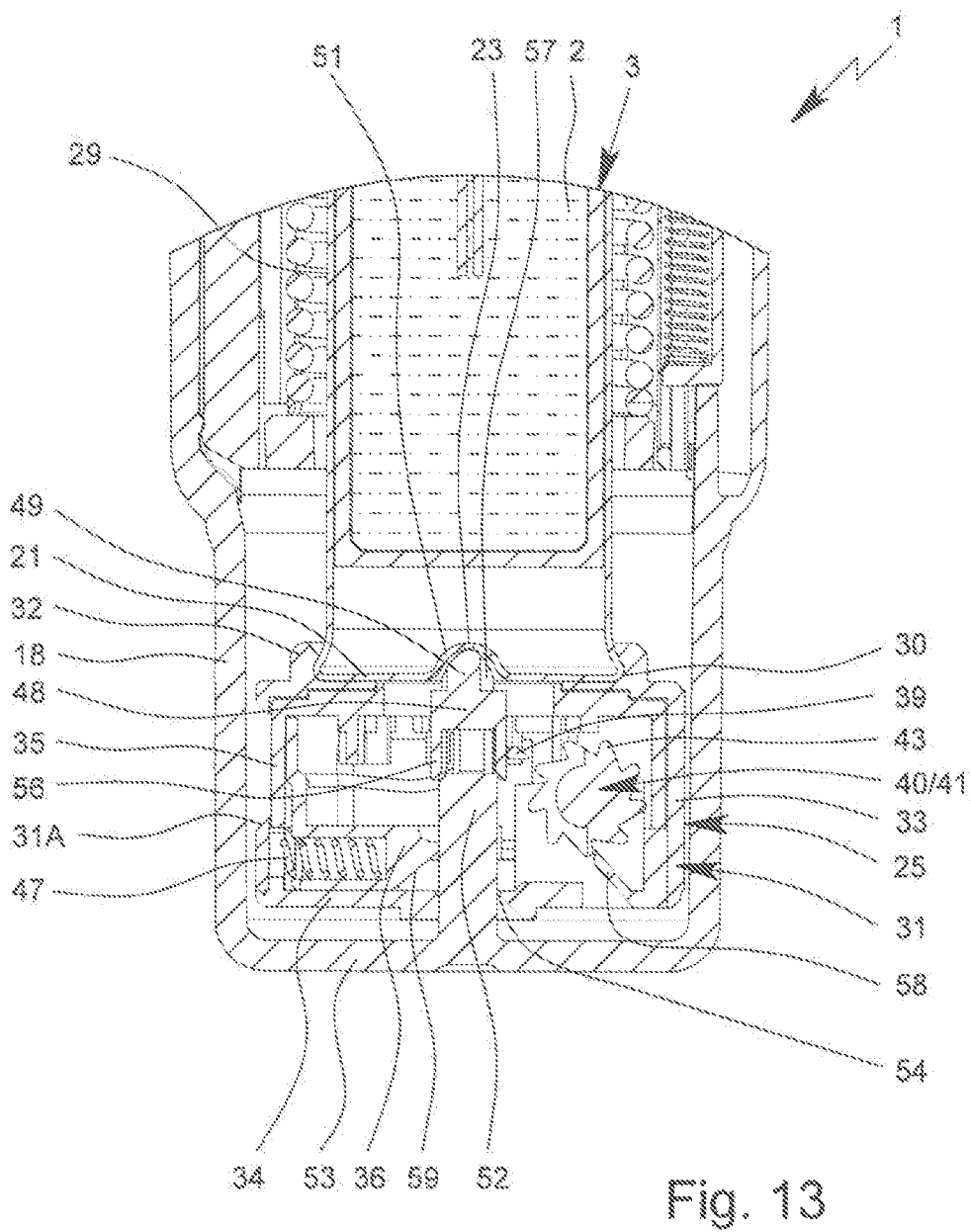

FIG. 13 shows in a similar enlarged section as FIG. 12 the fully tensioned state.

In the (fully) tensioned state, the container 3, more precisely the aeration opening or venting hole 23, is opened at least when the nebulizer 1 is tensioned with a container 3 for the first time.

Preferably, the opening of the container 3 or venting hole 23 for aeration is realized by piercing or breaking, in particular of foil 50.

Figure 1:
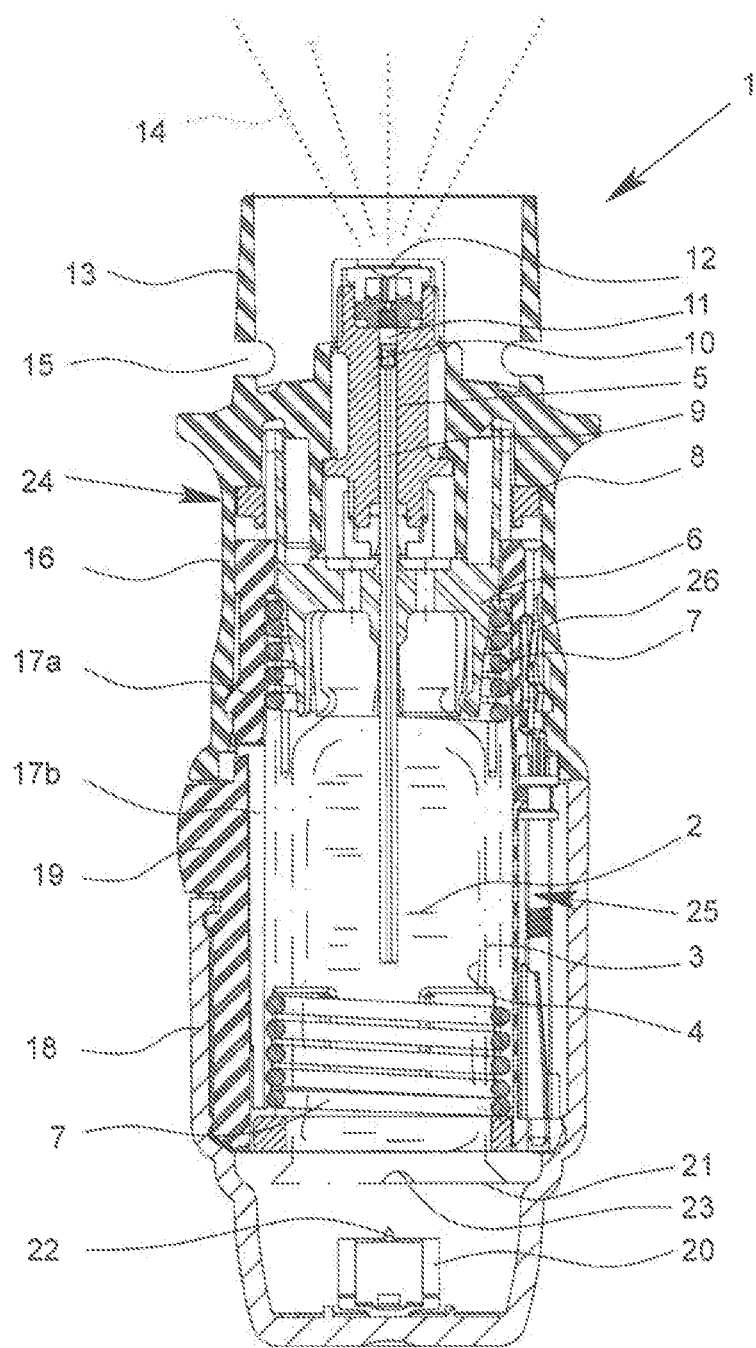
Figure 2:
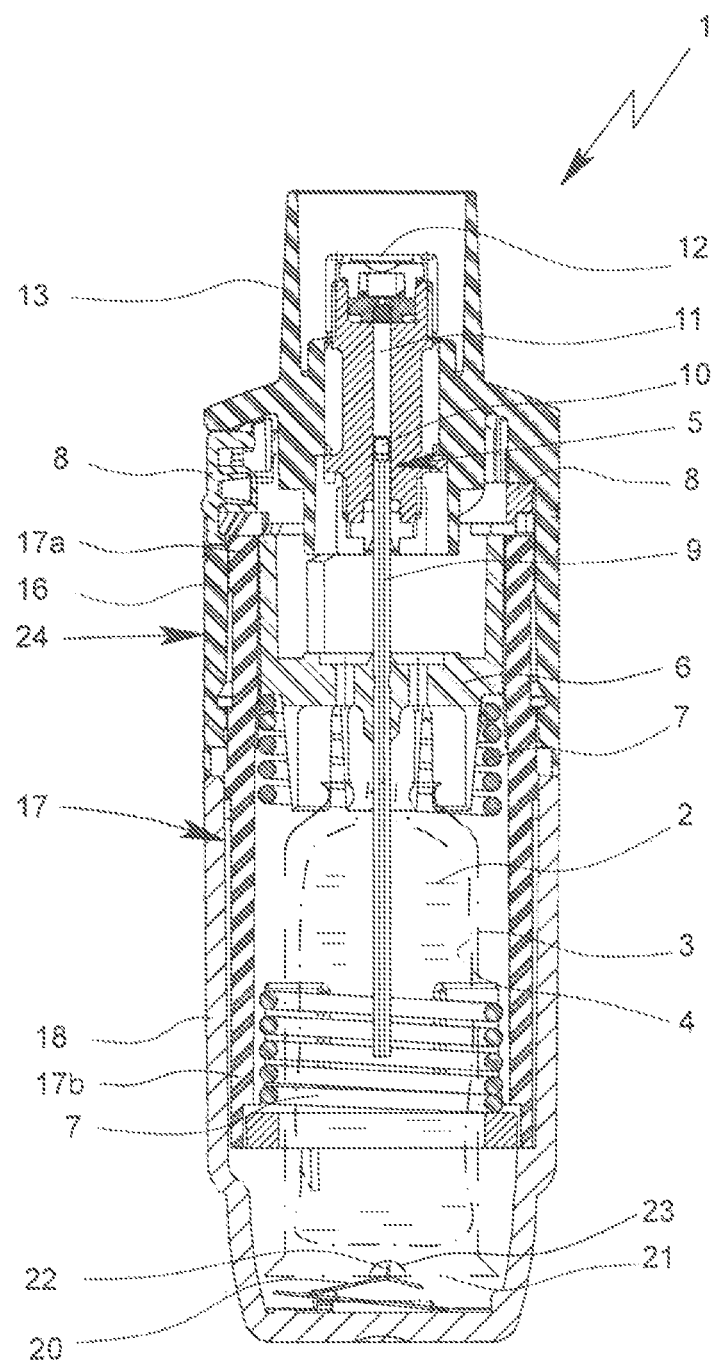
Figure 3:
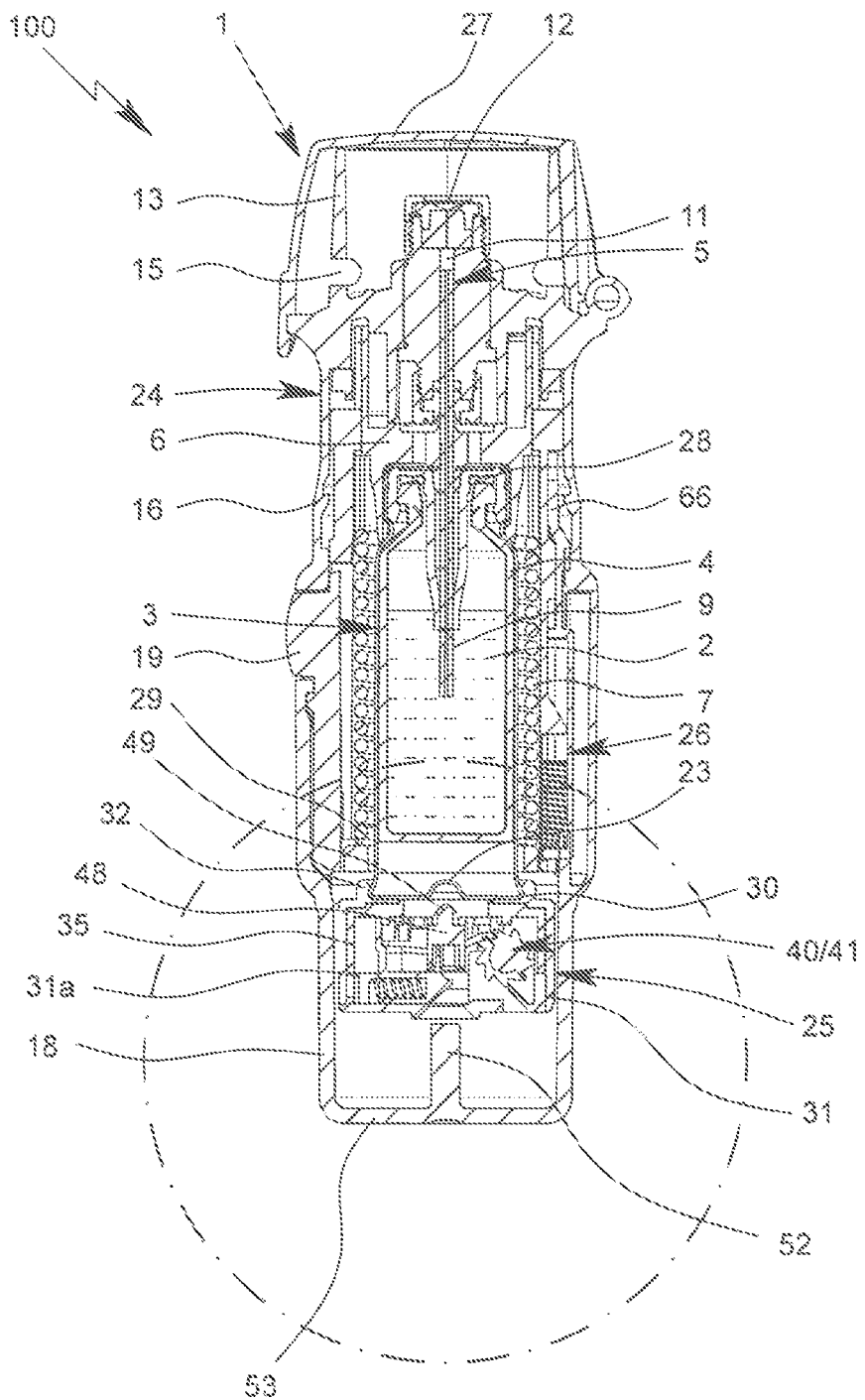

The opening or piercing can be effected directly by the driving part 52. Alternatively, the opening or piercing can be effected independently from the driving part 52, e.g. by means of the aeration spring 20 with the piercing element 22 similar to the embodiment shown in FIG. 2. Alternatively, as in the present embodiment, the opening or piercing can be achieved indirectly, preferably via the piercing part 48 which is preferably actuated by the driving part 52.

Preferably, the piercing part 48 is formed as separate part and/or provided by the indicator device 25 and/or arranged within the indicator device 25.

In the preferred embodiment, the piercing part 48 is held axially moveable by a support structure 55 of the indicator device 25, housing 31, upper part 32 and/or indicator element 35, as schematically indicated in FIGS. 10 and 11.

Preferably, the piercing part 48 and/or the support structure 55 are a one-piece-construction with a further part of the indicator devices 25, e.g. with the indicator element 35 or with the indicator housing 31, especially with the upper part 33 of the indicator housing 31.

Preferably, the piercing part 48, support structure 55 and the further part of the indicator device 25 are made of plastic in an injection molding process.

Preferably, the support structure 55 comprises flexible arms or ribs for holding the piercing part 48 axially moveable.

Alternatively the piercing part 48 can be constructed as separate, axially moveable part, which is optionally spring biased in the longitudinal or axial direction away from the container 3, so that the piercing tip 49 is retracted from the container 3 in the non-tensioned state.

It has to be noted that the piercing part 48 or its tip 49 is preferably received within the indicator device 25 or its housing 31, but can protrude outwards in the actuated state.

The opening or piercing can be repeated each time the nebulizer 1 is tensioned, i.e. each time when the container 3 reaches its end position in the tensioned state.

The piercing part 48 may be biased into its retracted or initial position shown in FIGS. 3 to 6, in particular by a preferably integrally formed biasing arm, spring or the like, preferably by the support structure 55.

The piercing part 48 may comprise a compensation portion, such as a flexible arm 56, for compensating any tolerances in axial direction. Such tolerances can occur in particular due to variations during production, in particular variations of the length of the container 3 and/or other components, variations of the connections of the container 3 with the indicator device 25, variations of the length of the indicator device 25 or its housing 31, variations of the axial position of the container 3 within the holder 6, and the like. Thus, different distances between the free end of driving part 52 and the counter-face of the piercing part 48 can result. The construction is such that the driving part 52 and the piercing part 48 cooperate in any case such that the desired piercing is ensured.

The compensation portion allows axial compression— here by radial flexing of arms 56—when a predetermined axial force is exceeded in order to avoid any damage of the container 3 and/or any other component of the nebulizer 1. Thus, in the preferred embodiment the driving part 52 first moves the piercing part 48 towards the container base 21 into the piercing position and further axial movement of the driving part 52 is compensated by the compensation portion, preferably by the flexible arms 56 being spread radially outwards, giving way to the tip of the driving part 52 for entering a central recess in the piercing part 48 (on the side opposite to the piercing tip 49).

The piercing part 48 comprises preferably at least one axial channel, in particular one or more axially extending grooves 57 circumferentially distributed around the circumference of tip 49, in order to ensure unblocked aeration or venting even if the piercing part 48 stucks or stays in the foil 50 or piercing position.

Figure 14:
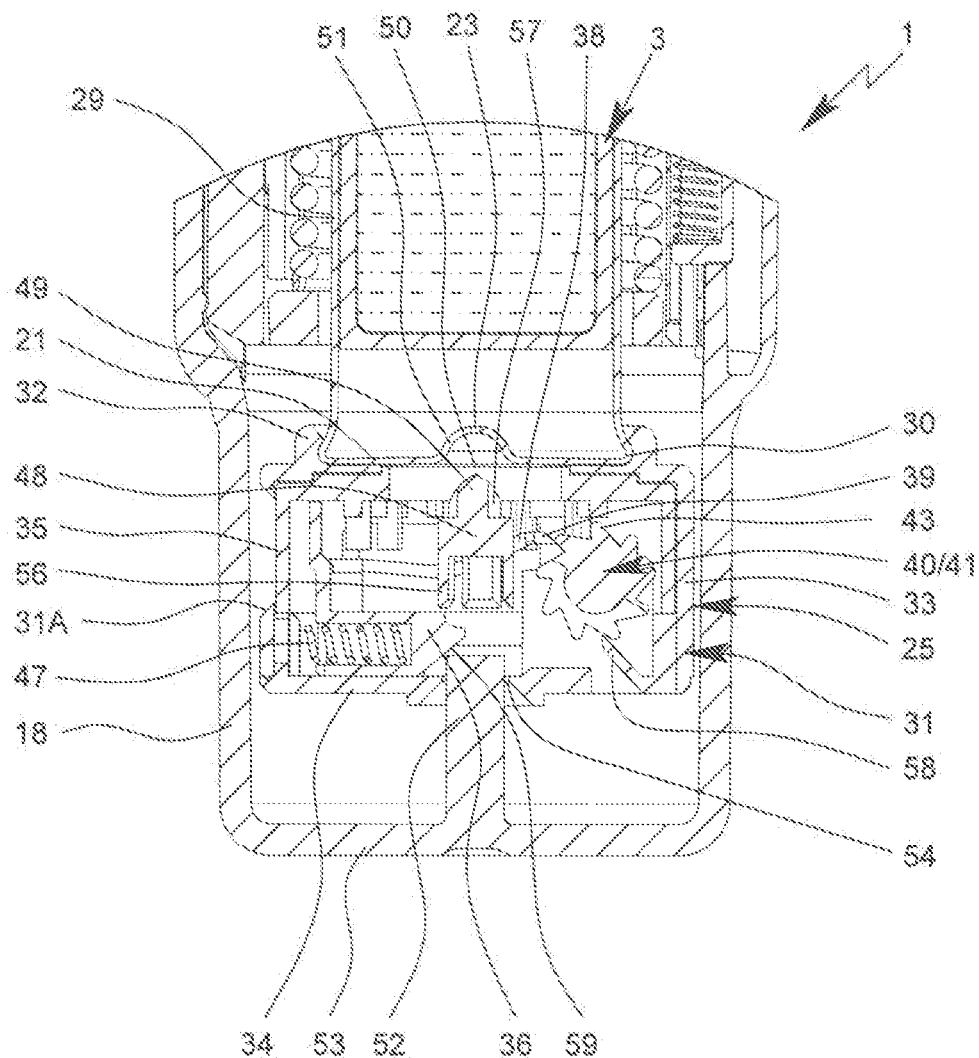

FIG. 14 shows in a similar enlargement as FIGS. 4, 12 and 13 an intermediate state of the pressurization or dispensing process, i.e. when the container 3 has been moved partially upwards again. In this state, the driving part 52 has been withdrawn from the indicator device 25 or through the insertion opening 54 partially such that the actuation element 36 starts to return to its initial or first position due to the force of the actuation spring 47. Finally, after sufficient withdrawal of the driving part 52, the actuation element 36 returns into the first position shown in FIGS. 3 to 6 when the back movement is completed.

The back movement of the container 3 and/or of the actuation element 36 actuates preferably the indicator device 25 or gear 41 and/or is detected or counted. In particular, the actuation element 36 or its arm 38 or actuation portion 39 transmits the back movement or movement from the second to the first position to the transmission 40. In particular, this movement causes an incremental rotation of gear 41.

Thus, in the present embodiment, the movement of the container 3 and/or indicator device 25 within the nebulizer 1 during dispensing is preferably used for actuating or triggering the indicator device 25 and/or for counting.

In the present embodiment, the actuation arm 38 or its portion 39 abuts against one tooth 43 of gear 41 during the back movement and, thus, turns the gear 41 due to the back movement one step further, in the drawings in clockwise direction.

Preferably, the indicator device 25 comprises a ratchet 58 preventing any counter-rotation of the transmission 40 or gear 41. Into the present embodiment, the ratchet 58 is formed by a flexible arm extending from the housing 31, in particular lower housing part 34, and/or meshing with or engaging into the gear 41 or its teeth 43.

In the end position, i.e. in the non-tensioned state, the driving part 52 is preferably further or completely retracted from the indicator device 25, the indicator housing 31 and/or insertion opening 54 as shown in FIGS. 3 to 6.

The transmission 40 or gear 41 transforms the actuation, in particular the (backward) movement of the actuation element 36 or its arm 38/actuating portion 39, into an indexing of the indicator element 35. The transmission ratio or transmission function of the transmission 40 or gear 41 may be designed or constructed such that a reduction or non-linear driving or indexing is achieved. In the present embodiment, the transmission 40 or gear 41 forms preferably a worm drive for achieving a desired reduction.

The movement of the actuation element 36—in particular from the first position to the second position—results in that the actuation arm 38 or its actuation portion 39 are moved out of engagement with the gear 41, in particular can be pulled over the next tooth 43. Hereby, the arm 38 is flexed out. The subsequent movement in opposite direction, i.e. the back movement or movement from the second to the first position, results in that the actuation arm 38 or its actuation portion 39 contacts the next tooth 41 and can transmit the at least essential linear movement of the arm 38, more precisely the preferably linear movement of the actuation element 36, into a rotation of the gear 41, more precisely in an indexing of gear 41 by preferably one tooth 43.

Preferably, the teeth 43 are asymmetrical, i.e. comprise differently inclined shoulders on one side and the other side in order to facilitate and/or ensure the incremental actuation and movement in one rotational direction by the back and forth movement and engagement of the actuation arm 38.

Preferably, the actuation element 36 is linearly moveable and/or forms a sliding carriage.

Preferably, the actuation element 36 is supported and/or held moveably by the housing 31, in particular lower part 34 of the housing 31. However, other constructional solutions are possible as well.

The actuation spring 47 acts preferably between the housing 31 or lower part 34 on one hand and the actuation element 36 on the other hand.

In the present embodiment, the spring 47 is preferably already compressed and/or biased in the first position and/or biases the actuation element 36 such that it at least partially closes or blocks the insertion opening 54.

Preferably, the actuation element 36 comprises an inclined gliding surface 59 at its part protruding into or over the insertion opening 32 in the first position. This surface 59 is inclined such that the insertion of the driving part 52, i.e. its axial movement or abutment, is transformed into a transversal or radial movement of the actuation element 36.

Alternatively or additionally, such a surface 59 can also be formed at the driving part 52 to achieve the desired transformation of the axial movement into a transversal or radial movement by means of an inclined plane.

Therefore, the actuation or rotation of the transmission 40 or gear 41 is preferably effected by the force of the actuation spring 47 or any other pressure or energy store or spring means. This results in the advantage that no additional force is necessary for driving the indicator device 25 or its indicator element 35. Consequently, the pressurization and dispensing process is not disturbed.

Further, the triggering of the counting or actuation of the transmission 40/gear 41 is effected preferably by the pressurization or dispensing process or movement, i.e. during the actual dispensing of fluid 2, i.e. usually during actual use or inhalation.

The actuation spring 47 biases the actuation element 36 preferably towards closing the insertion opening 54.

Usually, the movement of the actuation element 36 is restricted so that it does not completely close the insertion opening 54 before the locked state is reached. This limitation is realized in the present embodiment preferably via a control means or portion 62 against which a control part 63 abuts in particular to restrict the back movement of the actuation element 36 at the first position.

The abutment is shown in particular in FIG. 10. However, other constructional solutions are possible as well.

After the number of uses of the nebulizer 1 with the container 3 has reached or exceeded a predetermined number of uses as detected or registered by the indicator device 25, a locked state is entered and the nebulizer 1 will be locked against further use with the current container 3 and/or the container 3 will be locked against further use with the nebulizer 1.

In particular, the indicator device 25 comprises a blocking part 61 which blocks further use of the container 3 and/or closes or blocks the insertion opening 54 in the locked state as schematically shown in the schematically enlargement of FIG. 15 which shows a similar part as FIGS. 4 and 12 to 14. In this shown state, the container 3 has returned to its non-tensioned position and the driving part 52 has been retracted from the indicator device 25. During the last dispensing or pressurization process, the indicator device 25 has moved the indicator element 35 one step further and detected or registered that the predetermined number of uses has been reached or exceeded and, thus, that the locked state shall be entered.

In the present embodiment, the indicator element 35 comprises preferably a control portion 62 which releases the actuating element 36 for detection of the locked state which results in locking the nebulizer 1 or current container 3 against further use.

Preferably, the control portion 62 comprises a cut out or recess which allows or initiates movement of the blocking part 61 into a blocking position. Preferably, the blocking part 61 blocks or closes the insertion opening 54 in the blocking position, i.e. in the locked state. Preferably the control portion 62 is a wall or ridge on the inside of the rotatable indicator element 35.

Preferably, the blocking part 61 is integrated into the indicator device 25 or its housing 31.

The blocking part 61 is preferably moveable transversally or perpendicular to the longitudinal or dispensing direction of the container or nebulizer 1 and/or of the direction of stroke movement of the container 3.

Preferably, the blocking part 61 blocks the actuation or insertion movement of the driving part 52, in particular relative to the indicator device 25 and/or (sufficient) insertion of the driving part 52.

Preferably, the blocking part 61 is linearly moveable and/or formed by a sliding carriage. However, other constructional solutions are possible as well.

Preferably, the blocking part 61 is biased into its blocking position, in the present embodiment preferably by actuation spring 47 or any other suitable biasing means.

Preferably, the blocking part 61 closes or blocks the insertion opening 54 of the indicator device 25 after the last dose of fluid 2 has been dispensed and when the locked state has been entered or detected. This detection is preferably realized in that the blocking part 61 or any associated component, such as control part 63, can pass the control portion 62 in the locked state, most preferably by spring force, in particular by the force of actuation spring 47 or the like, as schematically shown in FIG. 11.

Preferably, the blocking part 61 is connected with or formed by the actuation element 36 or vice versa. Most preferably, the blocking part 61 forms a wall or side, preferably flat side, of the actuation element 36. However, other constructional solutions are possible as well.

In the present embodiment, the actuation element 36 can move in the locked state from the first position into the third position, i.e. preferably in the opposite direction than the movement into the second position.

In the present embodiment, the actuation element 36 can close the insertion opening 54 preferably completely in the third position (blocking position).

With other words, the blocking position of the blocking part 61 corresponds preferably to the third position of the actuation element 36.

Figure 15:
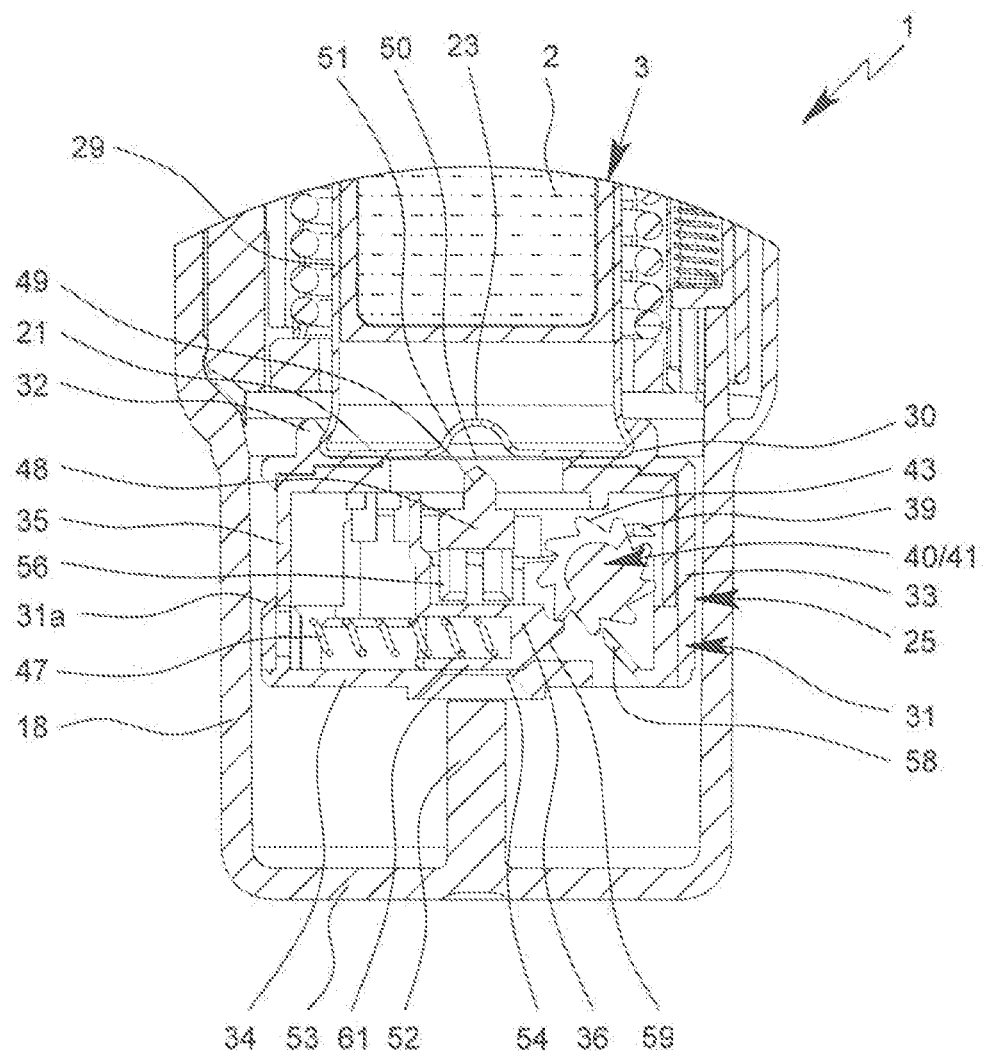

In the locked state or third position, the actuation element 36 has moved with the actuation arm 38 or its portion 39 further in the actuation direction so that the actuation portion 39 has passed the previous tooth 43 in the rotation direction of gear 41 as indicated in FIG. 15.

Preferably, the actuation element 36 is constructed to block further use of the container 3 in the locked state or third position (blocking position).

Preferably, the actuation element 36 is moveable back and forth between the first and second position for indexing the indicator element 35 and is moveable into a third position to block further use of the container 3 in the locked state.

In particular, the closed indicator device 25 or blocking part 61 results in particular in that the container 3 cannot move inside the closed housing of the nebulizer 1 in the stroke-like fashion as previously described and as required for normal or further use so that normal use is prevented.

In particular, the locking of the indicator device 25 or insertion opening 54 results in that the nebulizer 1 or housing part 18 is at least partially opened when the nebulizer 1 is tensioned once more or when it is partially tensioned. FIG. 16 shows this state (partially tensioned nebulizer 1 with partially opened housing part 18) in a schematic, longitudinal section of the nebulizer 1. During the tensioning process the container 3 is moving downwardly together with the indicator device 25. Starting from the non-tensioned state (upper position of the container 3), the indicator device 25 abuts soon with its blocking part 61/actuating element 36 against the member usually actuating the indicator device 25, here the driving part 52, so that a further usual downward movement is not possible.

In particular, the blocking part 61 restricts the axial moveability of the container 3 in the nebulizer 1 in the locked state, preferably by preventing the driving part 52 from insertion into the indicator device 25 or restricting its insertion in the locked state. Due to the force applied when tensioning the nebulizer 1 and due to the resulting axial force in the movement of the container 3, the housing part 18 will be moved outwards or relative to the nebulizer 1, inner part 17 or upper part 16 together with the container 3 and indicator device 25 during the further tensioning movement in axial direction in the locked state.

The above common downward movement of container 3, indicator device 25 and housing part 18 is possible due to a respectively constructed fastening of the housing part 18 at the nebulizer 1. In particular, the retaining force is selected or set such that it can be overcome by the downward movement of the container 3.

In the present embodiment, the retaining element 19 engages with a retaining nose 64 in a respective retaining recess 65 in the housing part 18 or vice versa. Thus, substantially an undercut or indention can be realized. However, the abutting shoulders which extend at least essentially radially of the nose 64 on one hand and the recess 65 on the other hand are slightly inclined, preferably by about 1° to 5° to the radial plane such that the axial force of the tensioning process can overcome the retaining force provided by the engagement of the nose 64 into the recess 65 so that the retaining element 19 is flexed radially and the retaining engagement is overcome. Consequently, the housing part 18 is moved downwardly as well and, thus, is pushed at least partly from the nebulizer 1 or separated from the upper housing part 16 and/or pushed from the inner part 17.

This pushing or axial displacement of the housing part 18 or any other opening of the nebulizer 1 results preferably in that the nebulizer 1 is locked against further use by means of the locking device 26. Therefore, the indicator device 25 or its blocking part 61 effects indirectly via the opening of the nebulizer 1 the desired locking of the nebulizer 1 in the locked state.

In the preferred embodiment, the locking device 26 blocks tensioning of the nebulizer 1 in the locked state.

Preferably, the locking device 26 comprises a moveable locking element 66 and an associated locking spring 67. The locking element 66 is preferably axially moveable between a locked position and an unlocked position. The locking element 66 is preferably biased into the locked position by the locking spring 67.

In the locked position, the locking element 66 is preferably in its lower axial position shown in FIG. 16. FIG. 17 shows an enlargement of the encircled area of FIG. 16.

In the locked position, the locking element 66 blocks rotation of the inner part 17 relative to the outer part 16 and, thus, blocks (further) tensioning of the nebulizer 1. This is preferably achieved in the present embodiment in that the locking element 66 moves or engages preferably axially into a respective pocket 68 formed in the upper part 16 such that said relative rotation is blocked. In particular, the locking element 66 engages with an engagement portion 69 into the respective recess or pocket 68 such that any further rotation and/or back rotation is prevented. However, other constructional solutions are possible as well.

The locking device 26, in particular the locking element 66 and the locking spring 67, are preferably arranged and/or supported by the inner part 17 and/or extend between the inner part 17 and upper part 16.

The nebulizer 1, inner part 17 or locking device 26 comprises preferably a cover element 70 covering the locking device 26 at least on the periphery of the lower part 17b of the inner part 17 in order to prevent or at least complicate any undesired manipulation of the locking device 26 or locking element 66 by a user or patient.

Figure 16:
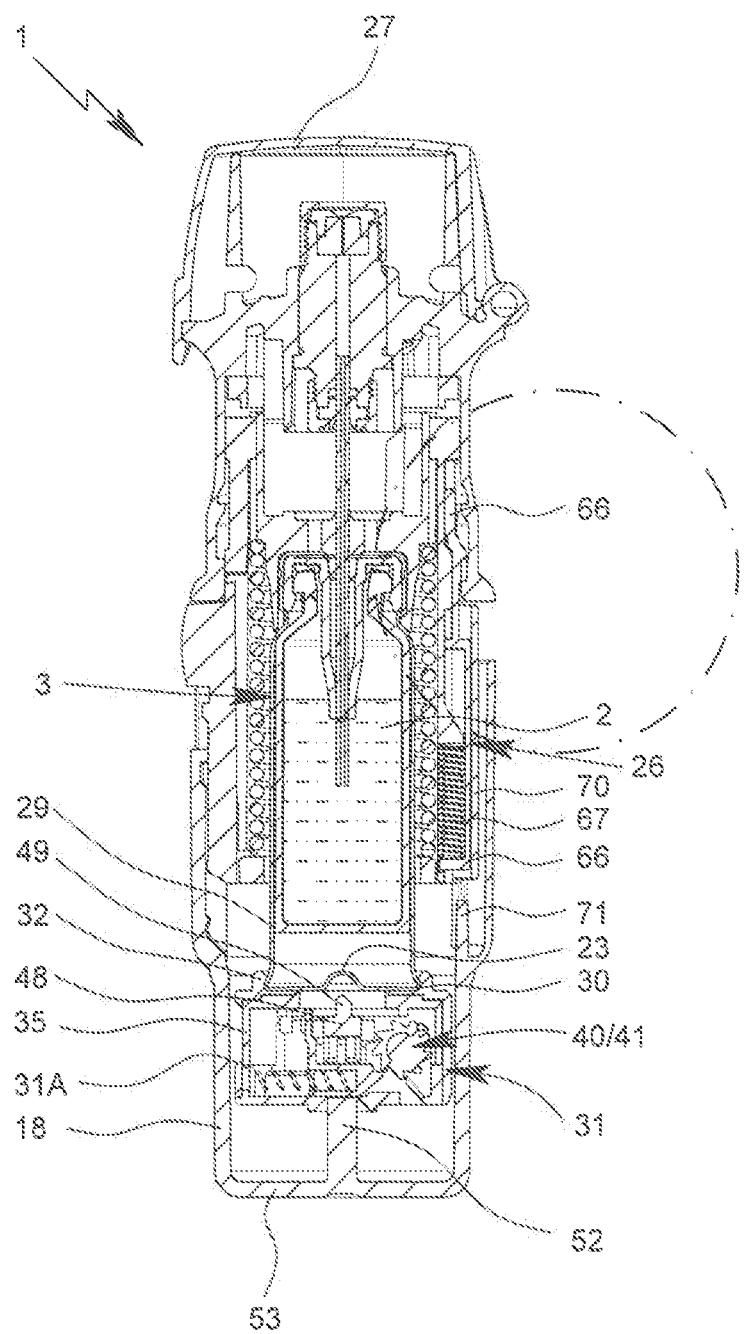
Figure 17:
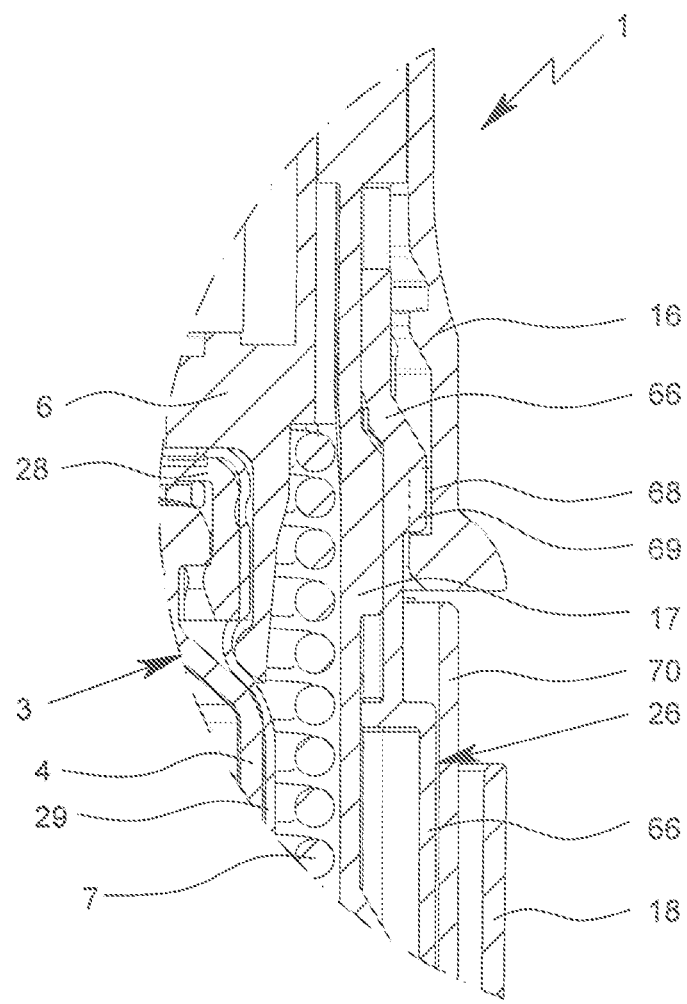
Figure 18:
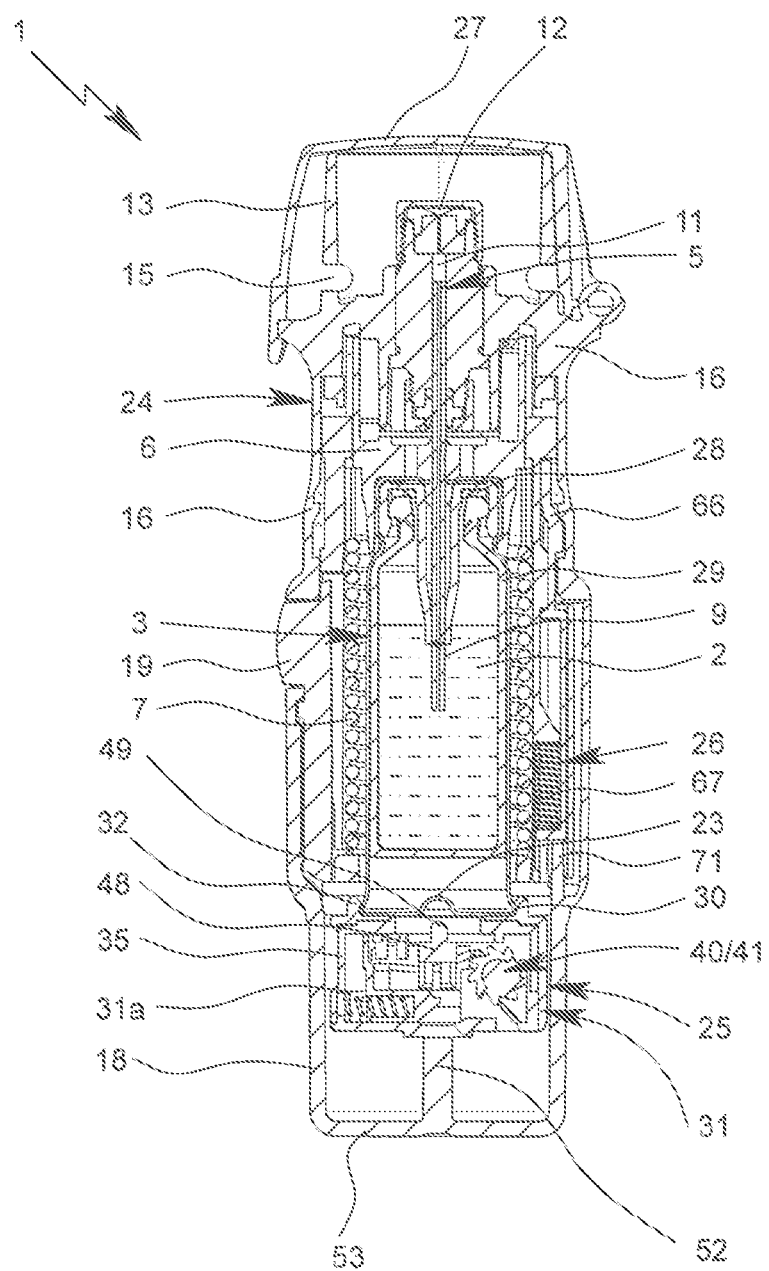

FIG. 18 shows the nebulizer 1 in a similar schematic section as FIG. 16, however with the locking device 26 in the unlocked position, i.e. the locking element 66 in the upper position. The locking device 26 or locking element 66 is brought into this position or unlocked preferably only by closing the nebulizer 1, in particular by the housing part 18 in the completely attached or closed position.

In the shown embodiment, the housing part 18 comprises a preferably finger-like and/or axially extending actuator 71 which extends into the locking device 66 and/or into the cover element 70 and/or axially abuts and/or pushes the locking element 66 into its unlocking position (upper position), as shown in FIG. 18. Thus, only the completely closed nebulizer 1 or housing part 18 unlocks the locking device 26 and, thus, unlocks the nebulizer 1.

The actuator 71 is preferably arranged within the housing part 18 so that any manipulation is not possible or at least complicated.

When the nebulizer 1 is in the locked state and, preferably when the nebulizer 1 or its housing part 18 has been opened partially by the last tensioning process, any further use of the nebulizer 1 with the container 3 and the indicator device 25 in its locked state is not possible. The locking device 26 locks preferably automatically. Preferably, the locking spring 67 biases the locking element 66 into the locking position, so that upon at least partial opening of the nebulizer 1 or (axial) displacement of its housing part 18, the locking device 26 or its locking element 66 can move and moves into the locking position.

Preferably, the locking element 66 is moveable (essentially or only) in axial direction.

After replacement of the current container 3 with its locked indicator device 25 (blocking part 61 in the blocking position) against a new container 3 including a new or reset indicator device 25, the nebulizer 1 or its housing part 18 can be closed completely again. Thus, the nebulizer 1 or its locking device 26 can be or is unlocked again. Preferably, the actuator 71 pushes the locking element 66 back into its unlocking position.

Thus, the locking device 26 is reset or unlocked again, preferably by (completely) closing the nebulizer 1, its housing 24 or housing part 18, and the nebulizer 1 can be used with the new container 3 as previously.

It has to be noted that the insertion opening 54, which is preferably arranged centrally and/or opens in axial direction and/or allows axial insertion of an actuator element, in particular the driving part 52 in the present embodiment, can also be formed as a recess, groove, indention or the like and/or can be arranged at any position or location at the indicator device 25 with any orientation.

Alternatively, the insertion opening 54 or its closing can also be omitted. Instead, the indicator device 25, actuation element 36 or blocking part 61 can more or less directly communicate with or actuate the locking device 26 or, for example, the retaining element 19 or blocking element 8 in order to cause a direct or indirect locking of the nebulizer 1 or container 3 against further use.

Figure 19:
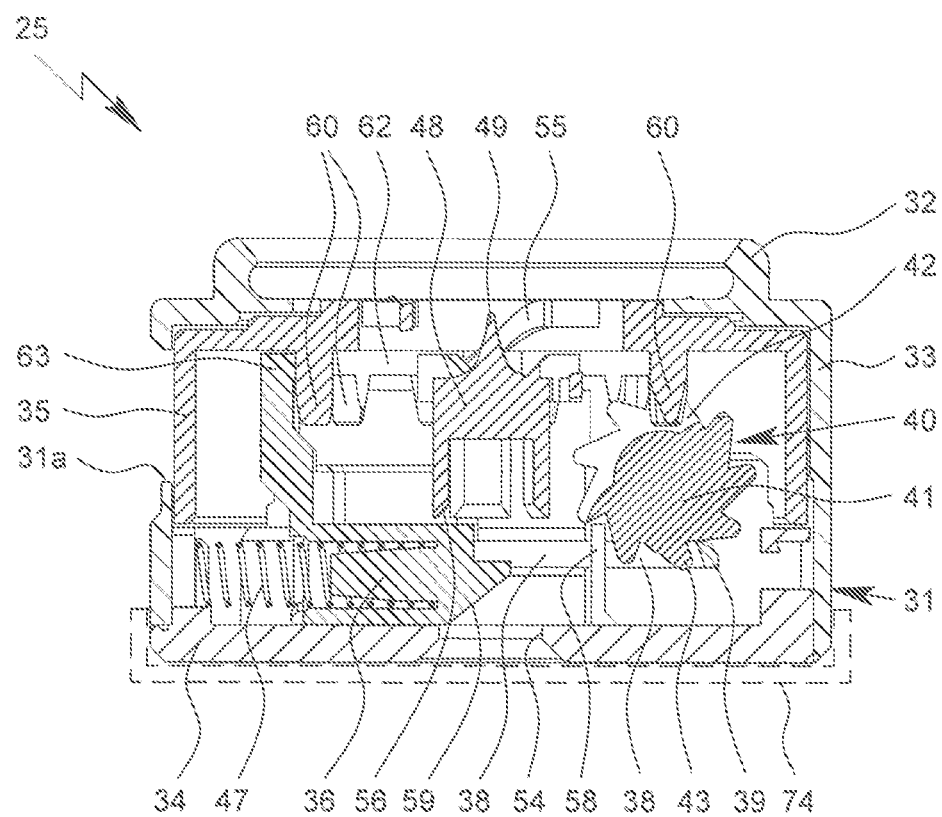
Figure 20:
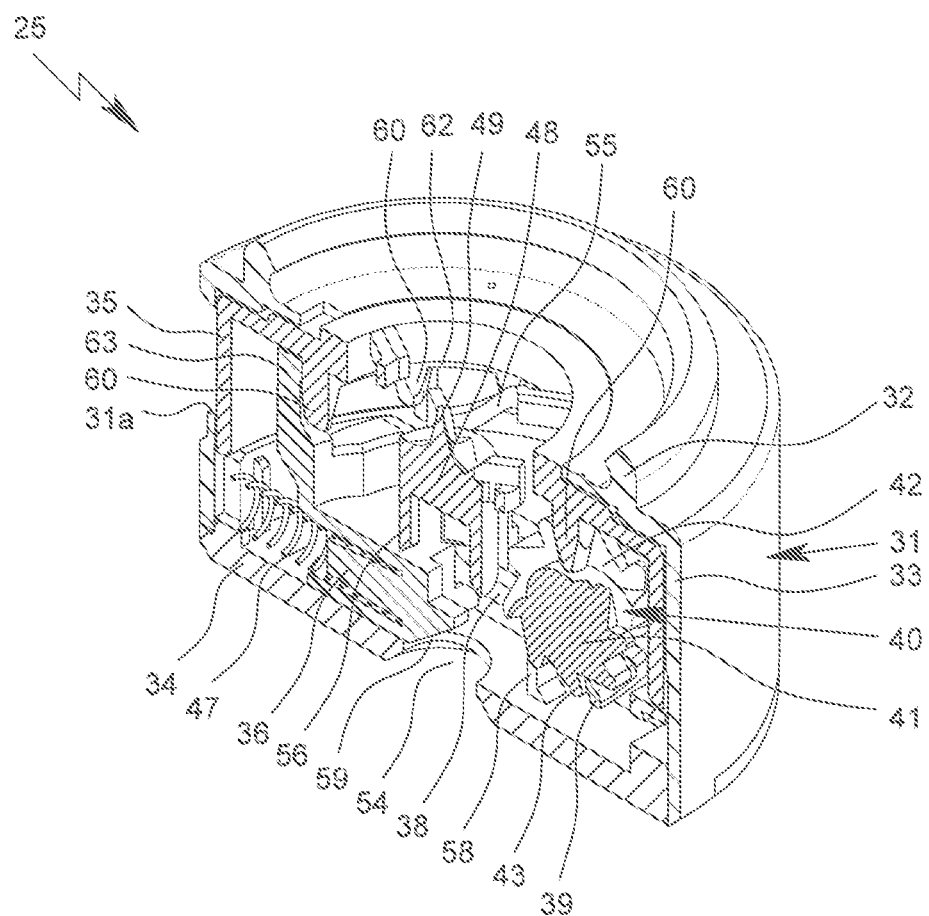

FIG. 19 shows in a schematic section the indicator device 25 according to a modified embodiment of the present invention. FIG. 20 shows a perspective view of the section according to FIG. 19.

In the following, only relevant differences are described so that the previous explanations and aspects apply in addition, in particular in the same or similar manner, without repetition.

In the modified embodiment, the actuation arm 38 and actuation portion 39 do not engage in between the worm drive, i.e. between the gear 41 and the engaging protrusions 60 of the driven part, here namely the indicator element 35, but engage with or actuate the gear 41 on another side or the side opposite the worm drive, here preferably in FIG. 19 from below and not from above. In particular, the actuation arm 38 extends more or less in a radial plane and/or more or less in a common plane with the actuation spring 47 and/or blocking part 61 or the sliding carriage part of the actuation element 36.

Preferably, the actuation arm 38 or portion 39 engages with the gear 41 on the side opposite the container 3 or gripping section 32.

In the modified embodiment, the indicator device 25 counts preferably when the nebulizer 1 is tensioned, i.e. during the tensioning process and not during the dispensing process as provided in the initial embodiment of the present invention.

In particular, the actuation element 36 or its arm 38 drives or rotates the transmission 40 or gear 41, when the driving part 52 is inserted into the indicator device 25, its housing 31 or its insertion opening 54 and/or when the actuation element 36 is moved from the first position to the second position and/or when the actuation element 36 is pushed transversally by the driving part 52. In the opposite direction, the actuation arm or its actuation portion 39 passes the next tooth 43 of the gear 41, i.e. does not drive the gear 41.

In the modified embodiment, the indicator device 25 or counting is not driven by the force of the actuation spring 47 or any other spring or energy store, but by the relative movement of the indicator device 25 within the nebulizer 1 or by the insertion of an actuator element, such as the driving part 52. However, other constructional solutions are possible as well.

In the modified embodiment, the blocking of the carriage/actuation element 36/locking part 61 to move into the third or locking position are released during the tensioning when a predetermined number of uses is reached or exceeded. Then, the carriage/actuation element 36/blocking part 61 abut against the driving part 52 because the counting occurs during the tensioning. When the nebulizer 1 is actuated or when the blocking element 8 is depressed, the nebulizer 1 is triggered and the (last) dose of fluid 2 is nebulized. During this nebulization, the driving part 52 is removed from the indicator device 25 or insertion opening 54 so that the carriage/actuation element 36/blocking part 61 are free to move into the third or locking position due to the force of the actuation spring 47 or any other spring means.

During the next tensioning, the nebulizer 1 or its housing 24 or housing part 18 will be partially opened when the driving part 52 abuts against the closed indicator device 25, in particular against the carriage/actuation element 36/blocking part 61 restricting or closing the insertion opening 54.

In the previous embodiment, the counting or actuating of the indicator device 25 takes place or occurs when dispensing fluid, i.e. when the driving part 52 is withdrawn from the insertion opening 54. There, the carriage/actuation element 36/blocking part 61 are released during the last use of the nebulizer 1 or dispensing, i.e. when moving from the second to the first position so that the carriage/actuation element 36/blocking part 61 can move further directly into the third or unlocking position. Thus, any later dispensing is not possible.

In both cases, i.e. in the previous embodiment and in the modified embodiment, the indicator device 25 blocks full axial or stroke-moveability of the container 3 within the nebulizer 1 in the locked state and/or causes at least partially opening of the nebulizer housing 24 and/or housing part 18 in the locked state, in particular when the nebulizer 1 is tensioned at least partially for the last time with the current container 3.

Further, the at least partial opening of the nebulizer 1 or its housing 24 or housing part 18 results in that the nebulizer 1 is blocked, in particular cannot be tensioned any further or used any further, with the current container 3.

FIGS. 19 and 20 show the indicator device 26 according to the present invention in the non-actuated or initial state and/or with the actuation element 36 in the first position. The control part 63, which extends preferably upwards and/or in axial direction, abuts against the preferably ring-like control portion 62 which is preferably formed by or at the indicator element 35. Preferably, the control portion 62 has a radial distance to the outer wall of the indicator element 35 so that the control part 63 can move in between and that the actuation element 36 is free to move between the first and second positions, while the abutment of the control part 63 against the control portion 62 prevents movement of the actuation element 36 from the first position further towards the third position and/or further to (complete) closing the insertion opening 54.

Preferably, the protrusions 60 are dent-like and/or are tapered towards its free ends.

Preferably, the protrusions 60 are formed on or connected with the control portion 62.

Generally, the insertion opening 54 is provided preferably with a conical surface or edge to facilitate insertion of the driving part 52 or the like.

Preferably, the support structure 55 forms or comprises one or more flexible arms for moveably holding the piercing part 48, preferably in the center of the indicator device 25 or its housing 31 or a respective opening of the housing 31, so that the piercing part 48 is usually held inside the indicator device 25 but can move and in particular protrude outwards and/or towards the container 3 for opening or piercing aeration. However, other constructional solutions are possible.

Generally, the indicator device 25 and the container 3 form an inseparable assembly or unit, which has to be replaced completely after use, in particular after reaching the locked state. However, it is also possible that the container 3 and indicator device 25 are supplied or offered as a kit which can be assembled by the use or patient.

Generally, the indicator device 25 cannot be reset after reaching the locked state so that it cannot be reused. However, it is also possible to modify the indicator device 25 such that it can be reset and reused. In this case, the indicator device 25 has to be separated from the present container 3 and connected with a new (unused) container 3. Most preferably, such a container change would automatically reset the indicator device 25.

Generally, the actuation element 36 or blocking part 61 is moveable preferably linearly, in particular like a sliding carriage. In particular, a sliding carriage is formed.

Preferably, the sliding carriage forms a base part of the actuation element 36 or blocking part 61.

Preferably, the sliding carriage, actuation element 36 or blocking part 61 is moveably held by sliding guides 72 on opposite sides, preferably on opposite sides of the insertion opening 54, as schematically shown in FIGS. 8 and 9. Preferably, the guides 72 are formed by respective rails or the like of the housing 31 or its lower part 34 which grip over respective edges or base portions 73 of the actuation element 36 or blocking part 61 to form the desired sliding guidance. However, other constructional solutions are possible as well.

Instead of the preferably linear or sled-like moveable actuation element 36 and/or blocking part 61, any other motion, in particular a radial and/or pivotal movement, is possible, in particular for partially or completely closing the insertion opening 54.

Alternatively, the actuation element 36 and/or blocking part 61 can move outwards from the indicator device 25 or its housing 31, preferably transversally and/or at one side of the indicator housing 31 for locking at least one engagement possibility and/or actuating any other component in the locked state or for locking the nebulizer 1 and/or container 3.

Alternatively or additionally, the actuation element 36 and/or blocking part 61 can engage into or abut against a section or contour of the housing part 18 and/or nebulizer housing 24 or the like in order to restrict or prevent operation or movement in the locked state in order to block further use of the nebulizer 1 and/or container 3 in the locked state.

The actuation element 36 and/or blocking part 61, in particular also when acting radially, are preferably biased by spring 47 or any other spring means. The spring or spring means can be formed integrally and/or by plastic parts or pieces. Alternatively, a spiral or clock spring or any other spring, such as helical spring 47 or the like, could be used for biasing the actuation element 36 and/or blocking part 61, preferably into the locked state.

It is also possible that the driving part 52 directly drives or actuates the gear 41. In this case, the driving part 52 is preferably elastically supported by the housing part 18, in particular via a spring means (not shown), in particular for compensating axial tolerances and/or allowing radial or transversal flexing of the driving part 52. Additionally or alternatively, the driving part 52 may be flexible in order to allow transversal flexing for engaging with the gear 41 only in one direction of relative axial movement to the gear 41 to rotate the gear 41 only in one rotational direction.

The indicator device 25 can comprise any other counting mechanism, in particular as described in WO 2009/037085 A1, page 4, line 19 to page 10, line 13, which is incorporated herein by reference. Such a counting mechanism can also trigger, release or actuate the actuation element 36 and/or blocking part 61. When using this counting mechanism, the rotatable indicator element 35 can also release or control the release of the carriage, actuation element 36 or blocking part 61 in the locked state to move into the third or locking position or close the insertion opening 54.

It is also possible that the carriage or blocking part 61 is independent from the counting. In particular, the driving part 52 may engage the hub of the counting mechanism shown in WO 2009/037085 A1 or the like and/or drive or actuate the indicator device 25 or counting without actuating the carriage or blocking part 61. In this case, the functions are separated. The carriage and/or blocking part 61 are preferably used only for restricting or closing the insertion opening 54 in the locked state, but not for actuating or driving the indicator device 25 of its counting mechanism or transmission 40 or indicator element 35 or the like.

The container 3 or indicator device 25 or insertion opening 54 may be provided with an optional protection 74, shown schematically only in FIG. 19, which covers in particular the insertion opening 54 before the first use.

Preferably, the protection 74 has to be removed before the container 3 and/or indicator device 25 can be inserted into the nebulizer 1 or housing part 18.

Preferably, the protection 74 extends transversally over the indicator device 25 or its housing 31 and/or over the container 3 and/or has a larger diameter than the indicator device 25 and/or container 3, in particular such that it does not fit into the nebulizer 1 or housing part 18.

Preferably, the protection 74 can be removed only irreversibly, i.e. cannot be reconnected after removal.

Preferably, the protection 74 covers or closes the insertion opening 54 and/or the indicator device 25.

Preferably, the protection 74 is connected to the indicator device 25 or container 3 by form-fit or force-fit and/or by a snap-fit or click-fit.

In the following, preferred aspects of the system 100, nebulizer 1, container 3 and indicator device 25 will be described in detail.

Figure 21A:
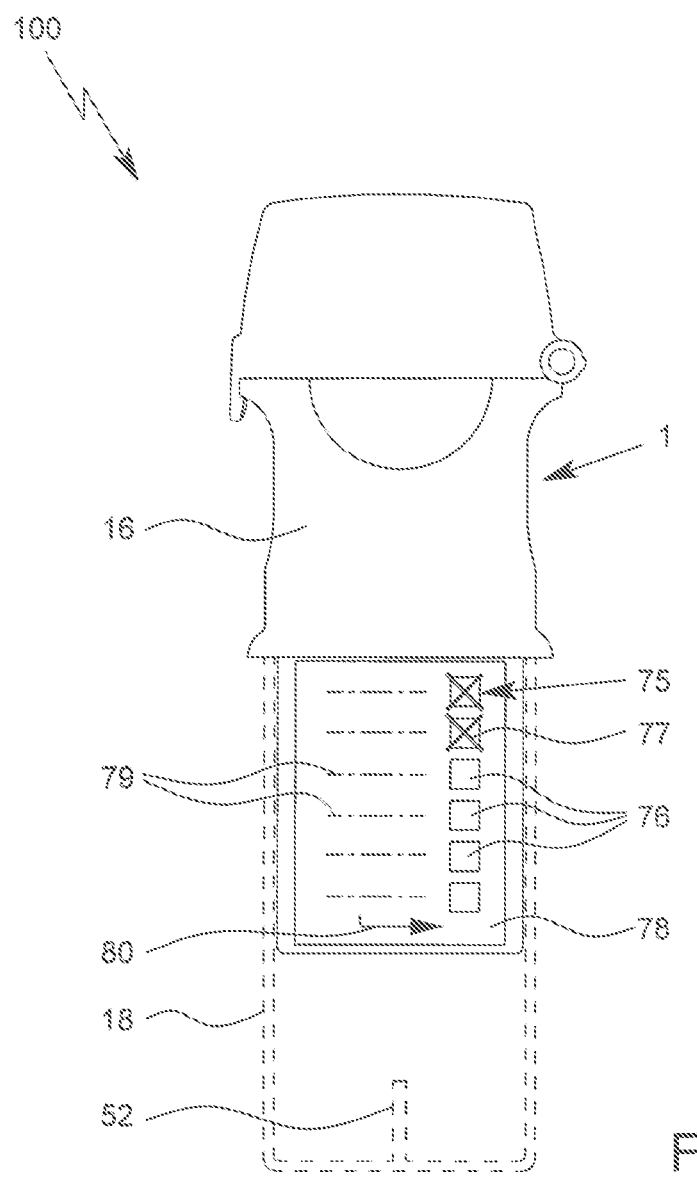
Figure 21B:
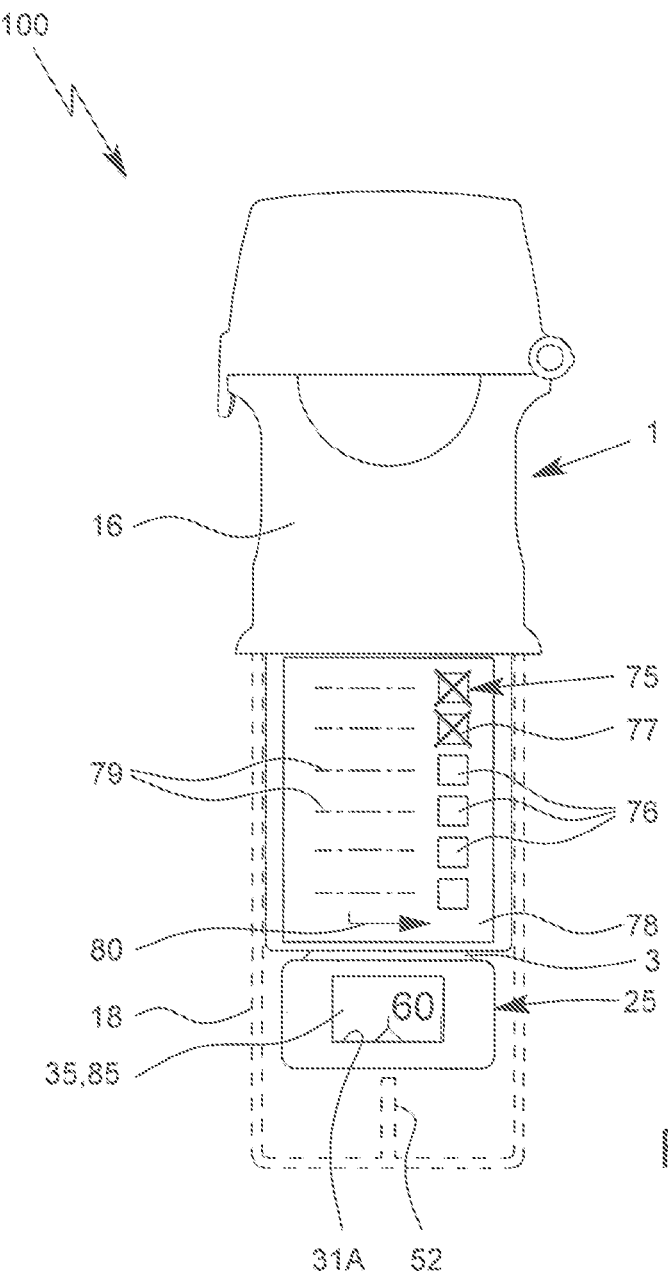

FIGS. 21A and 21B show in a schematic view the system 100 with the nebulizer 1 according to the present invention with an associated check scheme 75. Preferably, the system 100 or nebulizer 1 comprises, forms or supports the check scheme 75, in particular such that the check scheme 75 cannot be separated from the nebulizer 1 or a component of the nebulizer 1.

Preferably, the check scheme 75 is adapted to be marked, in particular each time a container 3 is inserted or replaced, to visualize the number of containers 3 already used or which still can be used with the nebulizer 1. With other words, the check scheme 75 is for marking the number of containers 3 already used or which still can be used, in particular so that it is visible when the maximum number of containers 3 to be used with the nebulizer 1 is approached or reached.

Preferably, the check scheme 75 comprises multiple check boxes 76, wherein the number of check boxes 76 corresponds preferably to the maximum number of containers 3 that can be used with the nebulizer 1 or that should not be exceeded. In particular, the check scheme 75 comprises not more than 10 check boxes 76. Preferably, the check scheme 75 comprises a number of 3 to 6 check boxes 75. Preferably, the multiple check boxes 76 are arranged as a group, in particular in a row/column or in a grid (i.e. in rows and columns). Such an arrangement ensures that a user can quickly access the information provided by the (marked) check boxes 76 by merely glancing at the check scheme 75.

Preferably, the term "check box" has to be understood in a broad sense to cover as well other, preferably predefined check areas for marking.

Preferably, there is an explanatory icon/symbol and/or a short explanatory text or heading in the vicinity and/or above the multiple check boxes 76. In particular, the explanatory icon/symbol or the short explanatory text or heading indicates how the check boxes 76 are to be used and/or what kind of event or number the user marks when marking a check box 76. An example for an explanatory text or heading is "container counter", "cartridge counter", "refill number" or the like.

The check scheme 75 or respective check boxes 76 are marked or provided with a mark 77 preferably each time when a new container 3 is inserted into or connected with the nebulizer 1.

In a preferred embodiment, the check areas or check boxes 76 contain (pre-printed) numerals (which can be crossed out, for instance). Preferably these numerals are arranged consecutively and/or range from 1 to the predetermined number of containers 3 to be used with the nebulizer 1. For instance, the check boxes 76 can thus be pre-numbered with numbers from 1 to 3 or 1 to 5 or 1 to 6 or 1 to 9 or the like.

In the shown embodiment, the first two check boxes 76 have been marked and, thus, indicate that the nebulizer 1 has been used with already two containers 3. It has to be noted that the currently connected or inserted (second) container 3 is not shown in FIG. 21A, but in FIG. 21B.

The check scheme 75 is preferably formed on or by a label 78. Preferably, it is printed on the label 78.

The check scheme 75 or label 78 is preferably attached to the nebulizer 1 or a component thereof, in particular to an accessible housing part, most preferably to the inner part 17.

Preferably, the check scheme 75 or label 78 is inseparable from the nebulizer 1 or housing part 17.

Preferably, the label 78 comprises—preferably readable or printed—information 79 and/or at least one symbol 80 for informing about the nebulizer 1, the fluid 2 and/or handling, e.g. by giving user information or handling instructions or the like. In particular, an arrow may be provided as symbol 80 in order to show the user how to tension the nebulizer 1, namely by rotating the (lower) housing part 18 together with the inner housing part 17 in the direction of the arrow.

Preferably, the check scheme 75 is covered or protected by a cover which is preferably transparent, at least in the area of the check scheme 75.

Preferably, the cover can be lifted or removed for marking the check scheme 75.

Preferably, the cover is formed by a component or any housing part of the nebulizer 1, most preferably by the housing part 18 which can be opened or detached for inserting or replacing the container 3.

Preferably, the housing part 18 is transparent so that the check scheme 75 and/or label 78 or respective information 79 and/or symbol 80 is visible for a user (not shown).

Preferably, the cover or housing part 18 covers the (lower end of) the container 3 and/or the indicator device 25 as well.

Preferably, the indicator device 25 or its indicator element 35 or display 85 is visible or readable through the cover or housing part 18 as well.

In particular, the user can read the check scheme 75 as well as the indicator device 25 through the cover or housing part 18 as schematically indicated in FIG. 21B which shows the nebulizer 1 with inserted container 3 including the indicator device 25. Thus, the user can easily see or notice all relevant information through the transparent cover or housing part 18, in particular without turning the nebulizer 1.

The nebulizer 1 has to be opened or the housing part 18 has to be detached for inserting or replacing the container 3. Then, the check scheme 75 or label 78 or the respective check box 76 is accessible and can be marked manually by the user.

Preferably, the check scheme 75 or label 78 or check boxes 76 can be marked by writing, in particular by means of a pen or pencil or the like (not shown).

Alternatively or additionally, the check scheme 75, respective check box 76 and/or label 78 can be marked by scratching. Thus, marking is possible even without any pen or pencil. Instead, the housing part 18, the (new) container 3 and/or its packaging as well as any other suitable object, such as a coin or the like, could be used for marking.

FIGS. 21A and 21B show as an example "X"-like crossings as marks 77. However, the marks 77 can have any suitable form and/or color. For example, scratching of the check scheme 75 or the check boxes 76 can result in respective color changes, e.g. when a cover layer is scratched away and a color below becomes visible.

Figure 22:
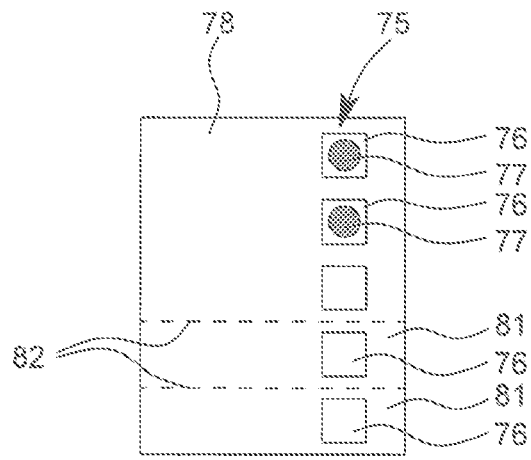

However, other or further possibilities for marking are explained in the following with reference to FIG. 22. FIG. 22 shows some alternatives or possible modifications of the check scheme 75 and label 78 in a schematic view.

The check scheme 75, respective check box 76 and/or label 78 can be marked alternatively or additionally by sticking label parts or the like as marks 77 on the check scheme 75, respective check box 76 or label 78 as schematically indicated in FIG. 22 for the above two check boxes 76. Such label parts can be provided or delivered with the respective container 3 that is inserted or its packaging.

Alternatively or additionally, the marking can be realized by partial removal of the check scheme 75 or label 78. For example, portions, such as tear portions 81, in particular with respective check boxes 76, can be torn or pulled or removed for marking. The (partial) removal can be facilitated by pull linkages 82 as schematically indicated in FIG. 22.

Alternatively or additionally, it is also possible to mark the check scheme 75 or respective check boxes 76 or label 78 by piercing or the like.

Alternatively or additionally, the check scheme 75, respective check box 76, the label 78 and/or respective marks can be made tactile or in braille or by embossed printing so that a blind person can read or detect the check scheme 75 or respective marks as well.

Figure 23:
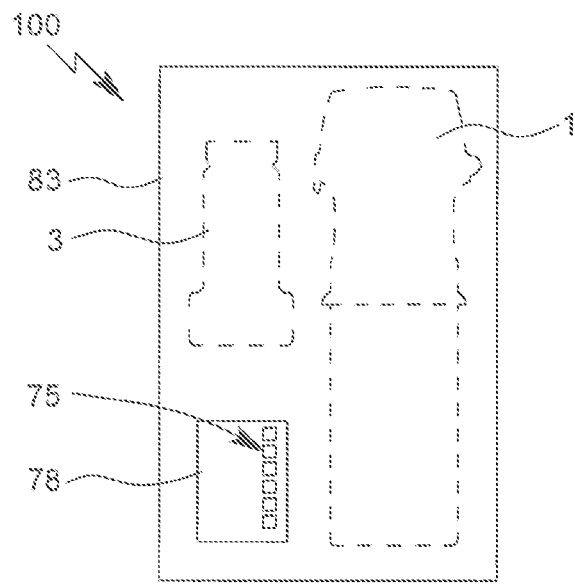

FIG. 23 shows in a schematic view a modified embodiment of the present invention. Here, a packaging or receptacle 83 for the nebulizer 1 and optionally a container 3 is used or provided with the proposed check scheme 75 and/or label 78. The check scheme 75 or label 78 can be arranged on the outside or inside and/or below a cover or the like.

Preferably, the packaging or receptacle 83 comprises the check scheme 75 and is used for indicating the number of containers 3 already used the nebulizer 1 or which still can be used with the nebulizer 1.

Figure 24:
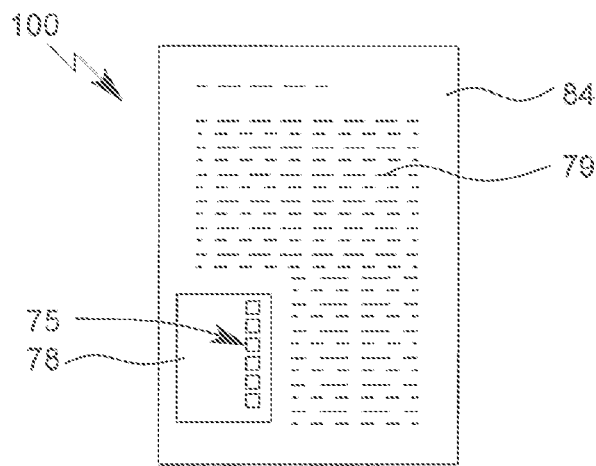

Alternatively or additionally, an outsert 84 can be provided with the check scheme 75 and/or label 78 as schematically indicated in FIG. 24.

The term "outsert" shall be understood in particular in the sense of an information leaflet relating to a pharmaceutical product or drug, in particular which is delivered with the nebulizer 1 and/or container(s) 3. Such information leaflet is usually attached or included or associated to a nebulizer 1 or container 3 as described.

The information leaflet or outsert 84 comprises preferably printed information 79 and according to the preferred embodiment also the check scheme 75.

It has to be noted that the provision or arrangement of the check scheme 75 at the nebulizer 1 is preferred in order to ensure availability of the check scheme 75. In particular, a user could discard the packaging 83 and/or outsert 84, but still use the nebulizer 1.

Preferably, the system 100 for nebulizing the fluid 2 comprises the nebulizer 1 for receiving a container 3 and optionally comprises at least one container 3, as schematically indicated in FIGS. 21A and 21B. The system 100 or nebulizer 1 comprises preferably the check scheme 75 or label 78 provided with the check scheme 75 as already explained.

Alternatively, the system 100 can comprise the packaging or receptacle 83 in addition to the nebulizer 1 and optionally at least one container 3 as schematically shown in FIG. 23. In this case, the nebulizer 1 or the packaging or receptacle 83 can be provided with or comprise the check scheme 75 or label 78 with the check scheme 75.

Optionally or alternatively, the system 100 may comprise the information leaflet or package insert or outsert 84 provided with the check scheme 75, in particular in addition to the nebulizer 1 and/or its packaging or receptacle 83, as schematically indicated in FIG. 24. In this case, the outsert 84 may comprise or form the check scheme 75 and/or may be provided with the label 78 including the check scheme 75.

Generally, the check scheme 75 or label 78 or information 79 can be provided with an identification or identification code, such as a bar code or QR code or the like, in particular as additional information, preferably for allowing identification of the nebulizer 1, the drug or fluid 2, the container 3, and/or the user.

In the following, further preferred aspects of the system 100, nebulizer 1, container 3 and/or indicator device 25 will be described with reference to the further Figs.

FIG. 25 shows in a very schematic, developed view a part of the outer or peripheral wall of the indicator element 35 or of a display (area) 85 formed thereof.

Preferably, the indicator device 25 or its indicator element 35, in particular the display 85, can indicate the number of uses performed or still possible with the associated container 3.

According to a preferred aspect, the indicator device 25, indicator element 35 or display 85 comprises or shows a color sequence 86, preferably a sequence of different colors, in particular of at least a first color area 86A, a second color area 86B and a third color area 86C.

Preferably, the display 85 begins with the first color area 86A, followed by the second color area 86B and ends with the third color area 86C.

Preferably, the darkness of the respective colors increase from the first area 86A to the third area 86C.

Preferably, the first color area 86A is relatively bright or light, in particular essentially white.

Preferably, the second color area 86B is slightly darker and/or essentially yellow.

Preferably, the third color area 86C is the darkest and/or essentially red. In particular, the third color area 86C comprises or is formed by a signal color and/or shading or the like providing a signal effect for clearly and/or intuitively indicating the user that the maximum number of uses of the container 3 and/or the locked state are approaching or reached.

Preferably, the first color area 86A is the longest in the direction of indexing.

Preferably, the second color area 86B is the shortest in the direction of indexing.

In particular, the second color area 86B is shorter than the length of the associated window 31A of the indicator device 25 in the direction of indexing so that in an intermediate position all three color areas 86A, 86B, 86C can be simultaneously seen from outside (compare FIG. 26C).

Preferably, the term "color sequence" has to be understood in a broad sense such that it also covers any sequence of areas 86A, 86B and/or 86C which appear different for the user, e.g. due to different shadings, color patterns or the like.

The indicator device 25, indicator element 35 or display 85 comprises or shows preferably a replacement symbol 87, such as an arrow or the like, for indicating a required container replacement.

The replacement symbol 87 is preferably red or arranged on or in a red area and/or third color area 86C.

Figure 25:
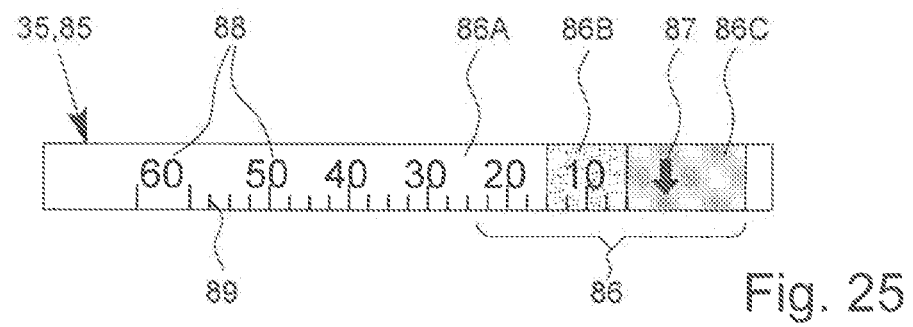

Preferably, the indicator device 25, indicator element 35 or display 85 comprises or shows further markings 37 in addition, such as numbers or numerals 88 and/or a scale 89 as schematically indicated in FIG. 25.

Preferably, the indicator device 25, indicator element 35 or display 85 is indexed or moved stepwise during each use or actuation, in particular tensioning or nebulizing, of the nebulizer 1.

Preferably, the indicator element 35 or display 85 or scale 89 does not provide a number or numeral 88 for each position or index step of the indicator device 25, indicator element 35 or display 85. In the present and preferred embodiment, the numbers or numerals 88 are provided e.g. for each 5th or 10th step or index position.

Generally, the indicator device 25 is adapted to let stepwise appear the color sequence 86, replacement symbol 87, numerals 88 and/or scale 89. This is preferably realized or achieved in that the indicator element 35 or display 85 is visible through at least one window 31A or optionally through two (preferably opposite) windows 31A, so that always only part of the indicator element 35 or display 85 is visible for the user.

In particular, the indicator element 35 or display 85 is moved or rotated or indexed stepwise below or relative to the window(s) 31A.

The indicator element 35 or display 85 can be provided with the markings 37, the replacement symbol 87, the numerals 88 and/or the scale 89 or any other symbols or signs in tactile form, braille or embossed printing to be detectable or tactile for a blind person. In particular, only part of the indicator element 35, display 85 or braille is tactile through the window 31A depending on the position of the indicator element 35.

The window 31A is preferably open and/or covered by a very thin and/or flexible foil or the like, so that a blind person can read the indicator device 25.

FIGS. 26A to 26D show in schematic view the container 3 with associated indicator device 25 in different states.

Figures 26A, 26B:
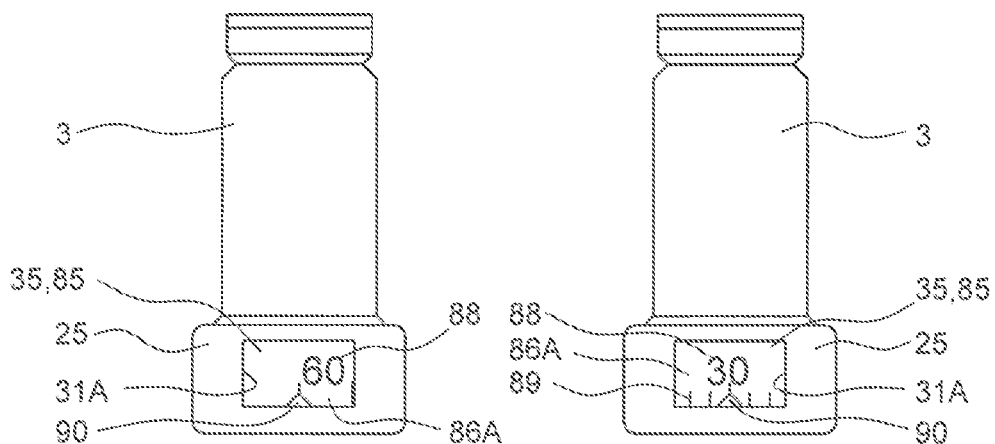

FIG. 26A shows initial state before first use.

As shown in FIG. 26, the indicator device 25 or its housing 31 or window 31A comprises preferably a reading mark 90 to facilitate (exact) reading of the indicator device 25, indicator element 35 or display 85, in particular of the numbers/numerals 88 and/or scale 89.

It has to be noted that the indicator device 25, indicator element 35 or display 85 shows preferably the number of uses which are still possible with the associated container 3. Accordingly, the display 85 starts with the indication of a high number which is decreasing depending on the uses. In this context, it has to be repeated that one use of the container 3 means that a dose of fluid 2 is discharged by means of the nebulizer 1 or that the nebulizer 1 is tensioned. This has to be distinguished from the term "used container" which relates to the locked state and means that the predetermined number of doses have been discharged and the container 3 cannot be or should not be used any further, but replaced.

FIG. 26A shows an initial state before first use. In particular, the indicator device 25, indicator element 35 or display 85 shows—here in or through window 31A—part of the first color area 86A and/or part of the display 85 before the usual begin of the numbers 88 and/or scale 89. This indicates that the nebulizer 1 should be tensioned and discharged multiple times until the first number, here "60" of the numbers 88 and/or the beginning of the scale 89 is aligned with the reading mark 90 before first inhalation. This preparation procedure ensures that any air is displaced out of the system of the nebulizer 1 before first inhalation so that precise metering is ensured.

FIG. 26B shows an intermediate state in the first color area 86A. Here, the number "30" of the numbers 88 is aligned with the reading mark 90. This indicates that the present container 3 can still be used 30 times, i.e. still 30 doses of fluid 2 can be discharged.

Figures 26C, 26D:
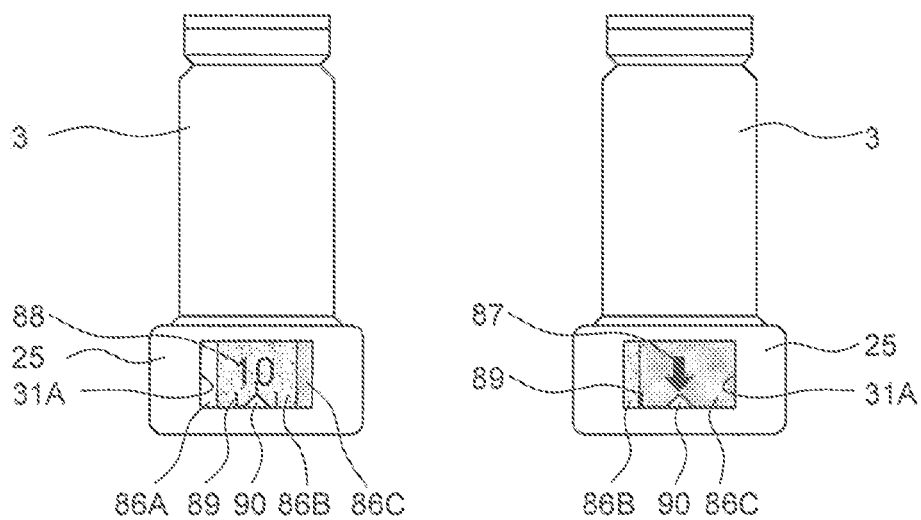

FIG. 26C shows a state when the end of use is approaching. Here, the second color area 86B is visible and, in addition, preferably the first color area 86A (on the left side) and the third color area 86C (on the right side) simultaneously. These colors visualize very prominently the intermediate state before the last color area 86C, i.e. the last phase of use starts.

FIG. 26D shows the final state. Starting from the intermediate state shown in FIG. 26C, the last or third color area 86C which is visible for the user increases with each use (discharge of fluid or tensioning of the nebulizer 1). Thus, the third color area 86C or the red color increases with each use.

Then, the replacement symbol 87 starts to become visible and starts to move towards as a center and/or reading mark 90, until the final state, namely locked state, is reached which is shown in FIG. 26D. In this state, the indicator device 25 locks or initiates locking of the locking device 26 or nebulizer 1, so that further use of the container 3 is prevented or blocked.

As already mentioned, individual features, aspects and/or principles of the embodiments described may also be combined with one another as desired and may be used particularly in the shown nebulizers 1 but also in similar or different nebulizers.

Features of the different embodiments can be combined or exchanged.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/115200 A1, preferably on pages 25 to 40, or in EP 2 614 848

A1, paragraphs 0040 to 0087, which are incorporated herewith by reference. In particular, these may be aqueous or non-aqueous solutions, mixtures, formulations containing ethanol or free from any solvent, or the like.

| List of reference numerals | |
|---|---|
| 1 | nebulizer |
| 2 | fluid |
| 3 | container |
| 4 | bag |
| 5 | pressure generator |
| 6 | holder |
| 7 | drive spring |
| 8 | blocking element |
| 9 | conveying tube |
| 10 | non-return valve |
| 11 | pressure chamber |
| 12 | nozzle |
| 13 | mouthpiece |
| 14 | aerosol |
| 15 | air supply opening |
| 16 | upper housing part |
| 17 | inner part |
| 17a | upper part of inner part |
| 17b | lower part of inner part |
| 18 | housing part (lower part) |
| 19 | retaining element |
| 20 | aeration spring |
| 21 | container base |
| 22 | piercing element |
| 23 | venting hole |
| 24 | nebulizer housing |
| 25 | indicator device |
| 26 | locking device |
| 27 | mouthpiece cover |
| 28 | head |
| 29 | container housing |
| 30 | container edge |
| 31 | indicator housing |
| 31a | window |
| 32 | gripping section |
| 33 | upper part |
| 34 | lower part |
| 35 | indicator element |
| 36 | actuation element |
| 37 | marking |
| 38 | actuation arm |
| 39 | actuation portion |
| 40 | transmission |
| 41 | gear |
| 42 | worm |
| 43 | tooth |
| 44 | axle section |
| 45 | bearing section |
| 46 | bearing portion |
| 47 | actuation spring |
| 48 | piercing part |
| 49 | piercing tip |
| 50 | foil |
| 51 | indention |
| 52 | driving part |
| 53 | bottom |
| 54 | insertion opening |
| 55 | support structure |
| 56 | flexible arm |
| 57 | groove |
| 58 | ratchet |
| 59 | surface |
| 60 | protrusion |
| 61 | blocking part |
| 62 | control portion |
| 63 | control part |
| 64 | retaining nose |
| 65 | retaining recess |
| 66 | locking element |
| 67 | locking spring |
| 68 | pocket |
| 69 | engagement portion |
| 70 | cover element |

| List of reference numerals | |
|---|---|
| 71 | actuator |
| 72 | sliding guide |
| 73 | base portion |
| 74 | protection |
| 75 | check scheme |
| 76 | check box |
| 77 | mark |
| 78 | label |
| 79 | information |
| 80 | symbol |
| 81 | tear portion |
| 82 | pull linkage |
| 83 | packaging/receptacle |
| 84 | outsert |
| 85 | display |
| 86 | color sequence |
| 86A | first color area |
| 86B | second color area |
| 86C | third color area |
| 87 | replacement symbol |
| 88 | numeral |
| 89 | scale |
| 90 | reading mark |
| 100 | system |

The invention claimed is:

1. A nebulizer (1) for nebulizing a fluid (2) and for receiving a plurality of replaceable containers (3) consecutively in series, each replaceable container (3) including a plurality of doses of the fluid (2) therein, the nebulizer (1) comprising:
a housing part (18) having detachment features facilitating repeated patient-detachment of the housing part (18) from the nebulizer (1) for the purpose of replacing each of the plurality of replaceable containers (3), and which: (i) when detached, provides access to an interior of the nebulizer (1) such that used ones of the plurality of replaceable containers (3) may be removed and replaced, and (ii) when re-attached, prevents access to the interior of the nebulizer (1), and completely surrounds and prevents access to the plurality replaceable containers (3),
a check scheme (75) for marking a number of containers (3) among the plurality of replaceable containers (3) already used or which still can be used;
a cover for covering the check scheme (75), wherein the housing part (18) includes the cover, such that: (i) the cover is detached from the nebulizer (1) in response to the patient-detachment of the housing part (18) from the nebulizer (1), (ii) the cover prevents access to the check scheme (75) when the housing part (18) is attached to the nebulizer (1), and (iii) the cover does not prevent access to the check scheme (75) when the housing part (18) is detached from the nebulizer (1),
wherein the cover includes at least a transparent portion positioned such that the patient may view the check scheme (75) through the housing part (18) when attached to the nebulizer (1),
wherein the check scheme (75) comprises multiple check boxes (76) for the patient to manually indicate each time a used one of the plurality of replaceable containers (3) is replaced, when the cover does not prevent access to the check scheme (75) when the housing part (18) is detached from the nebulizer (1),
wherein manual indication is a marking by at least one of writing, scratching, partial removal, and piercing.

2. The nebulizer according to claim 1, wherein the check scheme (75) is attached to the nebulizer (1) or inseparable from the nebulizer (1).

3. The nebulizer according to claim 1, wherein the check scheme (75) is attached to or formed on a further housing part (17) of the nebulizer (1).

4. The nebulizer according to claim 1, wherein the check scheme (75) is formed on or by a label (78).

5. The nebulizer according to claim 4, wherein the label (78) comprises in addition information (79) or at least one symbol (80) about the fluid (2) or use or handling of the nebulizer (1).

6. The nebulizer according to claim 1, wherein the cover permits the patient to see the check scheme therethrough.

7. The nebulizer according to claim 1, wherein one of:
the system (100) comprises a packaging or receptacle (83) which, in turn, comprises the check scheme (75), and
the system (100) comprises an outsert (84) which, in turn, comprises the check scheme (75).

8. The nebulizer according to claim 1, wherein:
each of the plurality of containers (3) include an indicator device (25) for automatically counting or indicating a number of uses performed or still possible with each of the plurality of containers (3), and
the indicator device (25) is adapted to let stepwise appear a color sequence (86) or replacement symbol (87) when approaching a predetermined number of uses or the end of use of the container (3), or that the indicator device (25) comprises a moveable or rotatable indicator element (35) with markings (37), a replacement symbol (87), numerals (88) or a scale (89) in tactile form, braille or embossed printing.

9. The nebulizer according to claim 8, wherein the indicator element (35) is rotatable or moveable stepwise with each use or below a window (31A) of the indicator device (25), such that respectively only part of the indicator element (35) is visible or tactile.

10. The nebulizer according to claim 8, wherein the indicator device (25) operates mechanically.

11. The nebulizer according to claim 1, wherein: each of the plurality of replaceable containers (3) comprises an indicator device (25) for counting or indicating a number (88) of uses performed or still possible with an operational container (3) among the plurality of replaceable containers (3), the indicator device (25) being adapted to let stepwise appear a color sequence (86) or replacement symbol (87) when approaching a predetermined number of uses or the end of use with the operational container (3).

12. The nebulizer according to claim 1, wherein: each of the plurality of replaceable containers (3) comprises an indicator device (25) with a moveable or rotatable indicator element (35) with markings (37), a replacement symbol (87), numerals (88) or a scale (89) in tactile form, braille or embossed printing.

* * * * *